(12) United States Patent
Dickson et al.

(10) Patent No.: US 12,012,439 B2
(45) Date of Patent: *Jun. 18, 2024

(54) TREATMENT OF MUSCULAR DYSTROPHIES

(71) Applicant: Royal Holloway And Bedford New College, Surrey (GB)

(72) Inventors: John George Dickson, Egham (GB); Linda Popplewell, Egham (GB)

(73) Assignee: Royal Holloway and Bedford New College, Surrey (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/212,244

(22) Filed: Jun. 21, 2023

(65) Prior Publication Data

US 2023/0391840 A1 Dec. 7, 2023

Related U.S. Application Data

(63) Continuation of application No. 16/770,358, filed as application No. PCT/GB2018/053521 on Dec. 5, 2018, now Pat. No. 11,725,032.

(30) Foreign Application Priority Data

Dec. 5, 2017 (GB) ...................... 1720224

(51) Int. Cl.
*C07K 14/47* (2006.01)
*C12N 15/86* (2006.01)

(52) U.S. Cl.
CPC .......... *C07K 14/4707* (2013.01); *C12N 15/86* (2013.01); *C12N 2750/14141* (2013.01)

(58) Field of Classification Search
CPC .............. A61K 48/005; A61K 48/0058; C07K 14/4707; C07K 14/4708; C12N 15/102;
(Continued)

(56) References Cited

U.S. PATENT DOCUMENTS

| 11,078,247 B2 | 8/2021 | Fotin-Mleczek et al. |
| 11,725,032 B2 * | 8/2023 | Dickson ............. C07K 14/4708 514/44 R |

(Continued)

FOREIGN PATENT DOCUMENTS

| EP | 2960336 A1 | 12/2015 |
| WO | 2016/177911 A1 | 11/2016 |
| WO | 2017/191274 A2 | 11/2017 |

OTHER PUBLICATIONS

Aug. 30, 2018—(UK) Search Report—App No. GB1720224.3.
(Continued)

*Primary Examiner* — Randall L Beane
(74) *Attorney, Agent, or Firm* — Banner & Witcoff, Ltd.

(57) ABSTRACT

There is described a nucleic acid molecule comprising a nucleotide sequence encoding a functional dystrophin protein. Also described is a vector, a host cell and a pharmaceutical composition comprising the nucleic acid molecule; use of the nucleic acid molecule in therapy, such as in the treatment of a muscular dystrophy; and a method of treating muscular dystrophy, the method comprising administering a therapeutically effective amount of the nucleic acid molecule to a patient suffering from a muscular dystrophy.

26 Claims, 7 Drawing Sheets

Specification includes a Sequence Listing.

(58) Field of Classification Search
CPC .......... C12N 15/86; C12N 2740/16043; C12N 2750/14141; C12N 2750/14143
See application file for complete search history.

(56) References Cited

U.S. PATENT DOCUMENTS

2019/0241633 A1  8/2019  Fotin-Mleczek et al.
2022/0025369 A1  1/2022  Fotin-Mleczek et al.

OTHER PUBLICATIONS

Human Gene Therapy, vol. 25, Feb. 2014, Koo et al., "Triple Trans-Splicing Adeno-Associated Virus Vectors Capable of Tranferring the Coding Sequence for Full-Length Dystrophin Protein into Dystrophic Mice", pp. 98-108.

Toby Maslin, Apr. 10, 2015, "Developing gene therapy for Duchenne muscular dystrophy", Muscular Dystrophy UK, [online], Available from: http://www.musculardystrophyuk.org.

Nucleic Acids Research, vol. 41, No. 17, Jul. 2013, Lorain et al., "Dystrophin rescue by trans-splicing: a strategy for DMD genotypes not eligible for exon skipping approaches", pp. 8391-8402.

Molecular Therapy, vol. 16, No. 11, Nov. 2008, Foster et al., "Codon and mRNA Sequence Optimization of Microdystrophin Transgenes Improves Expression and Physiological Outcome in Dystrophic mdx Mice Following AAV2/8 Gene Transfer", pp. 1825-1832.

Mar. 1, 2019—International Search Report—App No. PCT/GB2018/053521.

Jarmin et al., Expert Opinion, "New developments in the use of gene therapy to treat Duchenne muscular dystrophy" pp. 209-230, doi: 10. 1517/14712598.2014.866087. Epub Dec. 6, 2013.

Human Gene Therapy, vol. 23, Jul. 2012, Foster et al., "Genetic Therapeutic Approaches for Suchenne Muscular Dystrophy", pp. 676-687.

GenBank: LF450158.1, JP 2015516143-A/44529: Modified Polynucleotides for the Production of Proteins Associated With Human Disease (Oct. 28, 2016), available at https://www.ncbi.nlm.nih.gov/nuccore/LF450158.1/ (last visited Aug. 15, 2022) (Year: 2016).

Aug. 19, 2022—(US) Restriction and Election of Species Requirement—U.S. Appl. No. 16/770,358.

Nov. 3, 2022—(US) Non-Final Office Action—U.S. Appl. No. 16/770,358.

\* cited by examiner

TREATMENT OF MUSCULAR DYSTROPHIES

FIELD OF THE INVENTION

The present invention relates to a codon optimised dystrophin coding sequence. The invention also relates to vectors comprising the codon optimised dystrophin coding sequence, the use of the codon optimised dystrophin coding sequence in treating muscular dystrophies and methods of treating muscular dystrophies involving the codon optimised dystrophin coding sequence. Muscular dystrophies that can be treated include Duchenne muscular dystrophy (DMD).

REFERENCE TO AN ELECTRONIC SEQUENCE LISTING

The contents of the electronic sequence listing (sequence listing ST26.xml; Size: 29,000 bytes; and Date of Creation: Aug. 1, 2023) is herein incorporated by reference in its entirety.

BACKGROUND TO THE INVENTION

Duchenne Muscular Dystrophy is an X-linked inherited condition with an incidence of 1 in 3000-5000 boys. The DMD gene encodes dystrophin, a molecular linker between the intracellular actin and extracellular matrix, crucial to correct muscle contractility and integrity. In the absence of this protein, eccentric contractions result in muscle damage as contractile force may not be dissipated correctly, in the short-term muscle can be regenerated by satellite cells. Continued cycles of contraction and regeneration, propagates muscle fibrosis, scarring and ultimately lipid invasion. Initially this manifests within the proximal skeletal muscles of the limbs, reducing the child's mobility, before eventually progressing to respiratory and cardiac systems, requiring invasive support systems and ultimately causing death between the second and third decade of life.

Currently, the vast majority of gene and therapy approaches are focused upon the restoration of a shortened yet semi-functional dystrophin, producing a clinically lessoned, Becker muscular dystrophy phenotype by addressing specific patient mutations. Some of the current approaches include:

Truncated microdystrophin AAV vectors are in development for DMD gene therapy, but clearly key domains of the full-length protein have been removed and the microdystrophin may be sub-optimal in skeletal muscle, smooth muscle, heart, and CNS locations.

Antisense oligonucleotide approaches aiming to mask an mRNA splice site and facilitate the skipping of an exon. The major target is exon 51. However, due to the significant number of exons in which a mutation can occur, the therapeutic applicability of each antisense oligonucleotide is relatively low.

Multiplex CRISPR-mediated deletion across exons 45-55, thereby removing a major mutation hotspot. This is applicable to approximately 68% of patients.

NHEJ-mediated genome editing approaches whereby the microinsertions and deletions (InDels) occurring as a byproduct of the NHEJ DNA repair pathway are utilized in 1 in 3 cases to restore the reading frame.

A major limitation of these approaches is only certain patient cohorts can benefit from such therapies.

In view of the limitations in the current approaches, it would be preferable to develop a treatment approach which is more universal in nature so that it could be applied to a larger proportion of patients. Further, it would be advantageous if the whole dystrophin protein could be restored rather than a truncated form of it.

SUMMARY OF THE INVENTION

The inventors have designed an optimised cDNA sequence encoding full-length human dystrophin. This provides improved protein expression compared to the native wild-type human gene sequence.

Therefore, in a first aspect, there is provided a nucleic acid molecule comprising a nucleotide sequence encoding a functional dystrophin protein, wherein the nucleotide sequence has at least 77% identity to the sequence of SEQ ID NO. 1.

The optimised cDNA sequence encoding full-length human dystrophin has been shown to produce about a 22-fold increase in protein expression compared to the native sequence.

In a second aspect, there is provided a vector for expressing a dystrophin protein, the vector comprising the nucleic acid molecule described above. This means that the vector contains a nucleotide sequence encoding a functional dystrophin protein so that when this sequence is expressed, a functional dystrophin protein is produced by the cell in which the vector is contained.

In a further aspect, there is provided a pharmaceutical composition comprising a nucleic acid molecule or a vector as described above and one or more pharmaceutically acceptable excipients.

In additional aspects, there is provided the use of a nucleic acid molecule or a vector described above in therapy, for example, in the treatment of muscular dystrophies, and a method of treating muscular dystrophies comprising administering a therapeutically effective amount of a nucleic acid molecule or a vector as described above to a patient suffering from a muscular dystrophy.

DETAILED DESCRIPTION OF THE INVENTION

As indicated above, there is provided a nucleic acid molecule comprising a nucleotide sequence encoding a functional dystrophin protein, wherein the nucleotide sequence has at least 77% identity to the sequence of SEQ ID NO. 1.

The sequence of SEQ ID NO. 1 is a codon optimised nucleotide sequence encoding the full-length human dystrophin protein. The dystrophin nucleotide sequence was optimised by taking into account the following desired parameters: to avoid where applicable cis-acting motifs including internal TATA boxes, chi-sites and ribosomal entry, AT or GC rich sequence stretches, RNA instability motifs, repeat sequences and RNA secondary structures, and cryptic splice donor and acceptor sites in higher eukaryotes. The cDNA sequence alterations have the effect of increasing translational efficiency, mRNA stability, gene transcription and consequently protein synthesis, thus enhancing the level of transgene product per unit of gene transferred. As a result, this nucleotide coding sequence has surprisingly been found to produce about a 22-fold increase in protein expression compared to the native gene sequence. This increase was not expected by the inventors when producing the sequence.

Codon optimisation of sequences has been known for some time. However, the results of this have been mixed. Codon optimising any particular sequence does not necessarily result in an increase in protein expression. Often, expression is the same and sometimes worse compared to the native sequence. Further, where there is an increase in expression, the degree of improvement can also vary significantly, with an increase of less than 10-fold being quite common. As a result, when codon optimising a sequence, there is no expectation that this will result in an increase in protein expression, and there is certainly no expectation that this will result in an increase in expression of more than 5-10 fold. Certainly, you would not expect to achieve an increase of about 22-fold as for the sequence disclosed herein.

Further, there are a number of algorithms which are used in the codon optimisation of sequences and these different algorithms produce different sequences as a result of the optimisation process. These different sequences generally produce different levels of protein expression. However, no one algorithm consistently produces better results than the others. As a result, it is not possible to predict which codon optimisation algorithm will provide the best results for any particular sequence.

With regard to dystrophin, whilst groups have previously tried codon optimising microdystrophin constructs, the results of codon optimisation of full-length dystrophin has not been reported. Therefore, the approach used by the inventors is unconventional compared to other research in this area. Further, in view of the fact that no results have been reported on the codon optimisation of full-length dystrophin, there was no expectation that this approach would be successful, let alone produce the surprising results that have been demonstrated by the inventors.

The DMD gene, encoding the dystrophin protein, is one of the longest human genes known, covering 2.3 megabases (0.08% of the human genome). The primary transcript in muscle measures about 2,100 kilobases and takes 16 hours to transcribe. The mature mRNA measures 14.0 kilobases. The 79-exon muscle transcript codes for a protein of 3686 amino acid residues. Mutations in the DMD gene cause a number of muscular conditions, including Duchenne muscular dystrophy (DMD), Becker muscular dystrophy (BMD) and cardiomyopathy.

Previous attempts to address the mutations in the dystrophin protein have focused on producing shorter, partially functional dystrophin variants which can reduce the severity of the muscular dystrophy. Despite many efforts, delivery of the full-length dystrophin gene has not occurred with any convincing expression levels. Mainly this has been the result of the large transgene, limited delivery processes and the native sequence being sub-optimal for expression. However, it is thought that the optimised dystrophin construct with increased expression may produce high enough levels of dystrophin to ameliorate the clinical phenotypes from a relatively low level of correction. As a result, existing strategies to repair the dystrophin gene/deliver the transgene could be employed enabling a more 'universal' therapeutic strategy, thereby overcoming the current mutation specific constraints in many therapeutic strategies.

The nucleotide sequence has at least 77% sequence identity to the sequence of SEQ ID NO. 1. In some embodiments, the nucleotide sequence has at least 78% identity to the sequence of SEQ ID NO. 1. In various embodiments, the nucleotide sequence has at least 79% identity to the sequence of SEQ ID NO. 1. In further embodiments, the nucleotide sequence has at least 80% identity to the sequence of SEQ ID NO. 1. In some embodiments, the nucleotide sequence has at least 81% identity to the sequence of SEQ ID NO. 1. In other embodiments, the nucleotide sequence has at least 82% identity to the sequence of SEQ ID NO. 1. In particular embodiments, the nucleotide sequence has at least 83% identity to the sequence of SEQ ID NO. 1. In further embodiments, the nucleotide sequence has at least 84% identity to the sequence of SEQ ID NO. 1. In some embodiments, the nucleotide sequence has at least 85% identity to the sequence of SEQ ID NO. 1. In other embodiments, the nucleotide sequence has at least 86% identity to the sequence of SEQ ID NO. 1. In particular embodiments, the nucleotide sequence has at least 87% identity to the sequence of SEQ ID NO. 1. In further embodiments, the nucleotide sequence has at least 88% identity to the sequence of SEQ ID NO. 1. In some embodiments, the nucleotide sequence has at least 89% identity to the sequence of SEQ ID NO. 1. In further embodiments, the nucleotide sequence has at least 90% identity to the sequence of SEQ ID NO. 1. In some embodiments, the nucleotide sequence has at least 91% identity to the sequence of SEQ ID NO. 1. In other embodiments, the nucleotide sequence has at least 92% identity to the sequence of SEQ ID NO. 1. In particular embodiments, the nucleotide sequence has at least 93% identity to the sequence of SEQ ID NO. 1. In further embodiments, the nucleotide sequence has at least 94% identity to the sequence of SEQ ID NO. 1. In some embodiments, the nucleotide sequence has at least 95% identity to the sequence of SEQ ID NO. 1. In other embodiments, the nucleotide sequence has at least 96% identity to the sequence of SEQ ID NO. 1. In particular embodiments, the nucleotide sequence has at least 97% identity to the sequence of SEQ ID NO. 1. In further embodiments, the nucleotide sequence has at least 98% identity to the sequence of SEQ ID NO. 1. In some embodiments, the nucleotide sequence has at least 99% identity to the sequence of SEQ ID NO. 1. In other embodiments, the nucleotide sequence has at least 99.5% identity to the sequence of SEQ ID NO. 1. In particular embodiment, the nucleotide sequence has the sequence of SEQ ID NO. 1. In certain embodiments, the nucleotide sequence has the sequence of SEQ ID NO. 3.

The nucleotide sequence encodes a functional dystrophin protein. A functional dystrophin protein is one which can form part of a protein complex known as the costamere or the dystrophin-associated protein complex, which acts as a transmembrane platform that anchors the extracellular matrix (ECM) to the intracellular cytoskeleton. The dystrophin protein has four main functional domains: an actin-binding amino-terminal domain; a central rod domain; a cysteine-rich domain and a carboxyl-terminus. These bind to a number of structures/proteins to allow dystrophin to correctly carry out its function in the dystrophin-associated protein complex. For example, dystrophin binds to actin filaments, microtubules and a number of proteins which help to anchor the dystrophin at the sarcolemma. A skilled person would readily be able to identify whether a dystrophin protein is functional. For example, this could be done by using an assay involving immunohistochemical staining of treated muscle sections, staining for dystrophin, and looking for restoration of the dystrophin-associated protein complex at the sarcolemma through staining (see Counsell J R et al., Sci Rep. 7:44775 (2017); Koo T et al., Hum Gene Ther. 25(2):98-108 (2014); Koo T et al., Hum Gene Ther. 22(11): 1379-88 (2011); Le Guiner C et al., Nat Commun. 8:16105 (2017); and Meng J et al., Sci Rep. 6:19750 (2016)).

In preferred embodiments, the nucleotide sequence encodes a functional human dystrophin protein. The sequences of appropriate dystrophin proteins are well known to those skilled in the art. For example, a number of dystrophin isoforms are known. Therefore, the nucleotide sequence may encode a dystrophin protein selected from isoform 1 (identifier: P11532-2), isoform 2 (identifier: P11532-3), isoform 3 (identifier: P11532-4) and isoform 4 (identifier: P11532-1). Preferably, the nucleotide sequence encodes isoform 4 (identifier: P11532-1) of the human dystrophin protein. The amino acid sequence of the native human dystrophin protein can be found as SEQ ID NO. 2. Therefore, in some embodiments, the nucleotide sequence encodes a dystrophin protein having the amino acid sequence of SEQ ID NO. 2. Other dystrophin proteins that may be encoded by the nucleotide sequence include natural variants with mutations that do not affect the function of the dystrophin protein.

The human dystrophin protein is 3686 amino acids in length. Therefore, in some embodiments, the nucleotide sequence encodes a dystrophin protein having at least 3675 amino acids. In other embodiments, the nucleotide sequence encodes a dystrophin protein having at least 3680 amino acids. In further embodiments, the nucleotide sequence encodes a dystrophin protein having at least 3682 amino acids. In various embodiments, the nucleotide sequence encodes a dystrophin protein having at least 3683 amino acids. In certain embodiments, the nucleotide sequence encodes a dystrophin protein having at least 3684 amino acids. In particular embodiments, the nucleotide sequence encodes a dystrophin protein having at least 3685 amino acids.

In some embodiments, the nucleotide sequence encodes a dystrophin protein having at most 3697 amino acids. In other embodiments, the nucleotide sequence encodes a dystrophin protein having at most 3692 amino acids. In further embodiments, the nucleotide sequence encodes a dystrophin protein having at most 3690 amino acids. In various embodiments, the nucleotide sequence encodes a dystrophin protein having at most 3689 amino acids. In certain embodiments, the nucleotide sequence encodes a dystrophin protein having at most 3688 amino acids. In particular embodiments, the nucleotide sequence encodes a dystrophin protein having at most 3687 amino acids.

In particular embodiments, the nucleotide sequence encodes a dystrophin protein having about 3686 amino acids. In these embodiments, the nucleotide sequence can be said to encode a 'full-length' human dystrophin protein.

The nucleotide sequence encoding a dystrophin protein is preferably between 11,025 and 11,085 nucleotides in length. In some embodiments, the nucleotide sequence encoding a functional dystrophin protein is between 11,040 and 11,070 nucleotides in length. In other embodiments, the nucleotide sequence encoding a functional dystrophin protein is between 11,052 and 11,064 nucleotides in length. In particular embodiments, the nucleotide sequence encoding a functional dystrophin protein is about 11,058 nucleotides in length.

The nucleic acid molecule may comprise additional nucleotide sequences which encode further peptides/proteins or perform some further function, for example, aiding in the expression of the nucleotide sequence encoding the dystrophin protein. For example, the nucleic acid molecule may comprise a nucleotide sequence which encodes a green fluorescent protein (GFP) such that when the nucleic acid molecule is expressed, a dystrophin protein is produced which is tethered to the GFP.

Preferably, the nucleic acids described above are isolated.

It would be well with the capabilities of a skilled person to produce the nucleic acid molecules described above. This could be done, for example, using chemical synthesis of a given sequence with appropriate enzymatic ligation, where necessary.

The nucleic acid molecule can be any type of nucleic acid composed of nucleotides. The nucleic acid should be able to be expressed so that a protein is produced. Preferably, the nucleic acid is DNA or RNA. In some embodiments, the nucleic acid molecule is DNA, such as cDNA.

In a second aspect, there is provided a vector for expressing a dystrophin protein. The vector comprises the nucleic acid molecule described above. This means that the vector contains a nucleotide sequence encoding a functional dystrophin protein so that when this sequence is expressed, a functional dystrophin protein is produced by the cell in which the vector is contained.

In a therapeutic setting, the vector can take on a number of different forms depending on how the nucleic acid molecule is delivered to the cells of a patient suffering from a muscular dystrophy associated with a defective dystrophin protein. Various approaches are described in Chamberlain J R and Chamberlain J S ("Progress toward Gene Therapy for Duchenne Muscular Dystrophy", Mol Ther. 25(5):1125-1131 (2017)). For example, the nucleic acid molecule may be delivered by a transposon system (e.g. see Ley D et al., Stem Cell Res. 13(3 Pt A):390-403 (2014)), an artificial chromosome (e.g. see Tedesco F S, Chromosome Res. 23(1):135-41 (2015)), exploitation of the homology directed repair (HDR) DNA pathway (e.g. see Popplewell et al., Hum Gene Ther. (7):692-701 (2013)), a lentiviral vector (e.g. see Counsell J R et al., Sci Rep. 7(1):79 (2017)), or AAV vectors using a triple-transplicing approach (e.g. see Koo T et al., Hum Gene Ther. 25(2):98-108 (2014)).

In the triple-transplicing approach, the dystrophin cDNA is split across three adeno-associated viral vectors, which associate together in a directional manner when co-expressed due to corresponding splice acceptors and donors within each cassette. Alternatively, the sequence is split in three, each with a linked group 1 intron ribozymes, and each sequence expressed from an AAV vector leading to mRNAs which are spliced together in the correct order and orientation. Therefore, there is provided three AAV vectors, each containing a portion of the nucleic acid molecule described above, wherein following transduction of a cell with the three AAV vectors, the nucleic acid molecule is produced. In this context, the nucleic acid molecule may be produced as DNA or RNA (e.g. mRNA).

The exploitation of the homology directed repair (HDR) DNA pathway is a genetic engineering approach which involves production of a targeted DNA lesion in the DMD intron mediated by a specialised endonuclease and the exploitation of the HDR DNA pathway to integrate full-length dystrophin encoded by an exogenous cDNA donor.

In some approaches, stem cells may be isolated from a patient suffering from a muscular dystrophy associated with a defective dystrophin protein and these stem cells modified to incorporate the nucleic acid molecule described above, before the stem cells are reintroduced into the patient (e.g. see Zhu P et al., Mol Ther Nucleic Acids. 7:31-41 (2017) and Meng J et al., Sci Rep. 6:19750 (2016)). Alternatively, induced pluripotent stem cells may be used (e.g. see Gee P et al., Stem Cells Int. 2017:8765154 (2017)).

In certain embodiments in which the nucleic acid molecule is expressed by the vector (rather than being incorporated into the genetic material through a genetic engineering technique), the vector further comprises a promoter. The promoter causes expression of the nucleotide sequence encoding a functional dystrophin protein. Any appropriate promoter may be used, such as cytomegalovirus (CMV), Spc5.12, muscle creatine kinase (MCK), dMCK, tMCK, desmin (Des), alpha-myosin heavy chain (α-MHC), myosin light chain 2 (MLC-2), cardiac troponin C (cTnC) and slow isoform of troponin I (TnIS). Preferably, the promoter is a muscle specific promoter such as Spc5.12, muscle creatine kinase (MCK), dMCK, tMCK, desmin (Des), alpha-myosin heavy chain (α-MHC), myosin light chain 2 (MLC-2), cardiac troponin C (cTnC) and slow isoform of troponin I (TnIS).

In vectors which are designed to integrate the dystrophin coding sequence into the genetic material of a cell rather than simply express the dystrophin coding sequence, for example by exploiting the homology directed repair (HDR) DNA pathway, the vector may not contain the entire dystrophin coding sequence (although in some embodiments, it may). Instead, it may contain a fragment of the dystrophin coding sequence which is then integrated into the defective sequence to bring about correction of the dystrophin sequence. Importantly, the fragment of the dystrophin coding sequence must be long enough so that it replaces the part of the defective dystrophin sequence containing the disease causing mutation. In this approach, the fragment of the dystrophin coding sequence may be integrated after the first few exons of the naturally occurring sequence or even later in the dystrophin sequence. For example, the vector may contain exons 2-79, or shorter variants such as 45-79 or even 53-79.

Therefore, in some embodiments, there is provided a nucleic acid molecule comprising at least exons 53 to 79 of a nucleotide sequence encoding a functional dystrophin protein, wherein the nucleotide sequence has at least 77% identity to the sequence of SEQ ID NO. 1. Further, there may be provided a nucleic acid molecule comprising at least exons 45 to 79 of a nucleotide sequence encoding a functional dystrophin protein, wherein the nucleotide sequence has at least 77% identity to the sequence of SEQ ID NO. 1. In addition, there may be provided a nucleic acid molecule comprising at least exons 10 to 79 of a nucleotide sequence encoding a functional dystrophin protein, wherein the nucleotide sequence has at least 77% identity to the sequence of SEQ ID NO. 1. In various embodiments, the nucleic acid molecule comprises at least exons 9 to 79 of the nucleotide sequence encoding a functional dystrophin protein. In other embodiments, the nucleic acid molecule comprises at least exons 8 to 79 of the nucleotide sequence encoding a functional dystrophin protein. In certain embodiments, the nucleic acid molecule comprises at least exons 7 to 79 of the nucleotide sequence encoding a functional dystrophin protein. In some embodiments, the nucleic acid molecule comprises at least exons 6 to 79 of the nucleotide sequence encoding a functional dystrophin protein. In various embodiments, the nucleic acid molecule comprises at least exons 5 to 79 of the nucleotide sequence encoding a functional dystrophin protein. In other embodiments, the nucleic acid molecule comprises at least exons 4 to 79 of the nucleotide sequence encoding a functional dystrophin protein. In certain embodiments, the nucleic acid molecule comprises at least exons 3 to 79 of the nucleotide sequence encoding a functional dystrophin protein. In some embodiments, the nucleic acid molecule comprises at least exons 2 to 79 of the nucleotide sequence encoding a functional dystrophin protein. The nucleotide sequence described in this paragraph may have at least 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identity to the sequence of SEQ ID NO. 1 as described with respect to the full sequence above. This means that the nucleic acid molecule comprises at least exons 10 to 79 of a nucleotide sequence encoding a functional dystrophin protein, wherein the nucleotide sequence has at least 78%, 79%, 80%, etc. identity to the sequence of SEQ ID NO. 1. This also applies to the rest of the statements above, e.g. the nucleic acid molecule may comprise at least exons 53 to 79, at least exons 45 to 79, at least exons 9 to 79, at least exons 8 to 79, at least exons 7 to 79, etc. of the nucleotide sequence encoding a functional dystrophin protein. Also provided is a vector comprising the nucleic acid molecule described above.

In some embodiments, the vector described above is a Puc57-human DMD intron 1 plasmid repair template as depicted in FIG. 6. In various embodiments, the vector described above is a lentiviral human DMD intron 1 plasmid repair template as depicted in FIG. 7.

The invention also provides a host cell comprising any one of the nucleic acid molecules or vectors described above. Preferably, the vector is capable of expressing the dystrophin nucleotide sequence in the host. The host may be any suitable host.

As used herein, the term "host" refers to cells which harbour a nucleic acid molecule or a vector, as well as cells that are suitable for use in expressing a recombinant gene or protein. It is not intended that the present invention be limited to any particular type of cell. Indeed, it is contemplated that any suitable cell will find use in the present invention as a host. A host cell may be in the form of a single cell or a population of similar or different cells, for example in the form of a culture (such as a liquid culture or a culture on a solid substrate). In some embodiments, the host cell may be a stem cell. This may be an autologous human stem cell or an induced pluripotent stem cell.

The host cell may permit the expression of the nucleic acid molecule. Thus, the host cell may be, for example, a bacterial, a yeast, an insect or a mammalian cell. Suitable mammalian cells may be from a human, a non-human primate, a rodent, especially a mouse, or may be canine, feline, ovine or porcine. Where the mammalian cell is a human cell, such as a stem cell, it is preferably isolated.

In one aspect, the invention provides a pharmaceutical composition comprising a nucleic acid molecule or a vector of the invention and one or more pharmaceutically acceptable excipients. The one or more excipients include carriers, diluents and/or other medicinal agents, pharmaceutical agents or adjuvants, etc.

The invention also provides a method of treating a muscular dystrophy, the method comprising administering a therapeutically effective amount of a nucleic acid molecule or a vector as described above to a patient suffering from the muscular dystrophy. Preferably, the patient is human.

The muscular dystrophy is associated with a mutation in the DMD gene. The muscular dystrophy may be selected from Duchenne muscular dystrophy (DMD), Becker muscular dystrophy (BMD) and cardiomyopathy.

When the muscular dystrophy is "treated" in the above method, this means that one or more symptoms of the muscular dystrophy are ameliorated. It does not mean that the symptoms of the muscular dystrophy are completely remedied so that they are no longer present in the patient, although in some methods, this may be the case. The method of treating results in one or more of the symptoms of the muscular dystrophy being less severe than before treatment.

A "therapeutically effective amount" refers to an amount effective, at dosages and for periods of time necessary, to achieve the desired therapeutic result, such as raising the level of (functional) dystrophin in a subject (so as to lead to dystrophin production at a level sufficient to ameliorate the symptoms of the muscular dystrophy).

Further, the invention provides the nucleic acid molecule encoding a functional dystrophin protein as described above, or a vector as described above for use in therapy, for example, in the treatment of a muscular dystrophy.

In addition, the invention provides the use of the nucleic acid molecule encoding a functional dystrophin protein as described above or a vector as described above in the manufacture of a medicament for treating a muscular dystrophy.

The invention also provides a method for delivery of a nucleotide sequence encoding a functional dystrophin protein to a subject, which method comprises administering to the said subject a nucleic acid molecule encoding a functional dystrophin protein as described above or a vector as described above.

In the description above, the term "identity" is used to refer to the similarity of two sequences. For the purpose of this invention, it is defined here that in order to determine the percent identity of two nucleotide sequences, the sequences are aligned for optimal comparison purposes (e.g., gaps can be introduced in the sequence of a first nucleic acid for optimal alignment with a second nucleic acid sequence). The nucleotide residues at nucleotide positions are then compared. When a position in the first sequence is occupied by the same nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length. A sequence comparison is typically carried out over the entire length of the two sequences being compared.

The skilled person will be aware of the fact that several different computer programs are available to determine the identity between two sequences. For instance, a comparison of sequences and determination of percent identity between two sequences can be accomplished using a mathematical algorithm. In a preferred embodiment, the percent identity between two nucleic acid sequences is determined using the sequence alignment software Emboss Stretcher (www.ebi.ac.uk/Tools/psa/emboss_stretcher) using the following pairwise alignment options: Matrix: DNAfull; Gap open: 16; Gap extend: 4; and Output format: Pair. An alternative option is to use Clone Manager 9 (Sci-Ed software—www.scied.com) using global DNA alignment; parameters: both strands; scoring matrix: linear (mismatch 2, OpenGap 4, ExtGap 1).

Alternatively, the percent identity between two nucleic acid sequences can be determined using the Needleman and Wunsch (1970) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. A further method to assess the percent identity between two nucleic acid sequences can be to use the BLAST sequence comparison tool available on the National Center for Biotechnology Information (NCBI) website (www.blast.ncbi.nlm.nih.gov), for example using BLASTn for nucleotide sequences using the default parameters.

All patent and literature references cited in the present specification are hereby incorporated by reference in their entirety.

BRIEF DESCRIPTION OF THE DRAWINGS

The invention will now be described in detail by way of example only with reference to the figures which are as follows.

****p<0.0001 (unpaired t-test). Sequence optimisation produced a 17-fold increase in expression.

Figure 6:
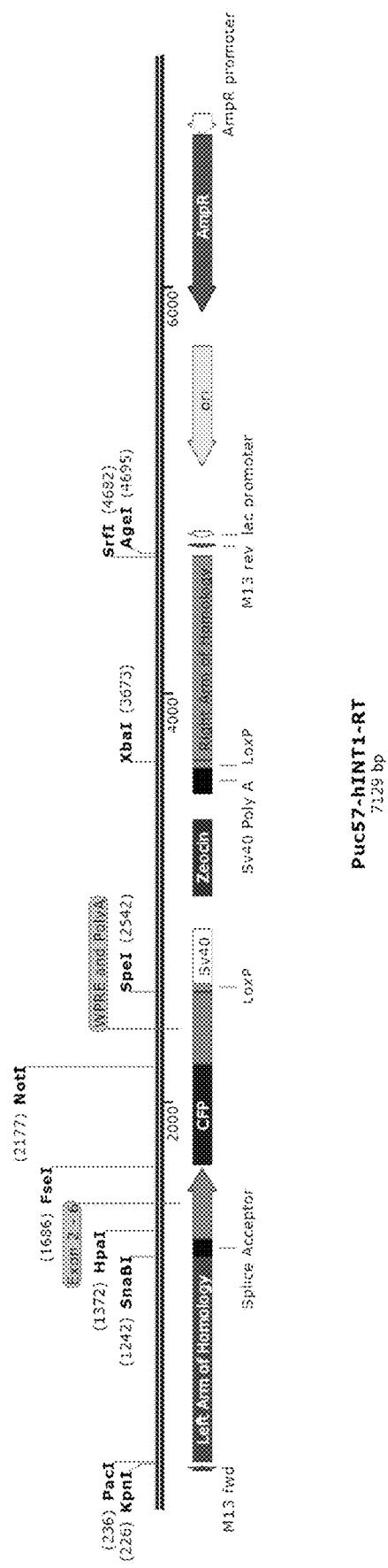

FIG. 6: A linear schematic of the Puc57-human DMD intron 1 plasmid repair template. A linear schematic of Puc57-hINT1-RT empty vector. The FseI and NotI sites flanking the Cyan fluorescent marker, serve as the directional cloning sites for the optimised full-length dystrophin. Upstream of this cloning site is a 1 kb left arm of homology, synthetic beta globin splice acceptor and Exons 2-6 of optimised DMD cDNA. Downstream of this cloning sequence is the WPRE and polyA to enhance expression. Followed thereafter by a floxed zeocin cassette, to facilitated selection and a 1 kb right arm of homology. Where possible these constituents are flanked by unique restriction sites that are annotated, ensuring that the repair template is amenable to changing constituents if required.

Figure 7:
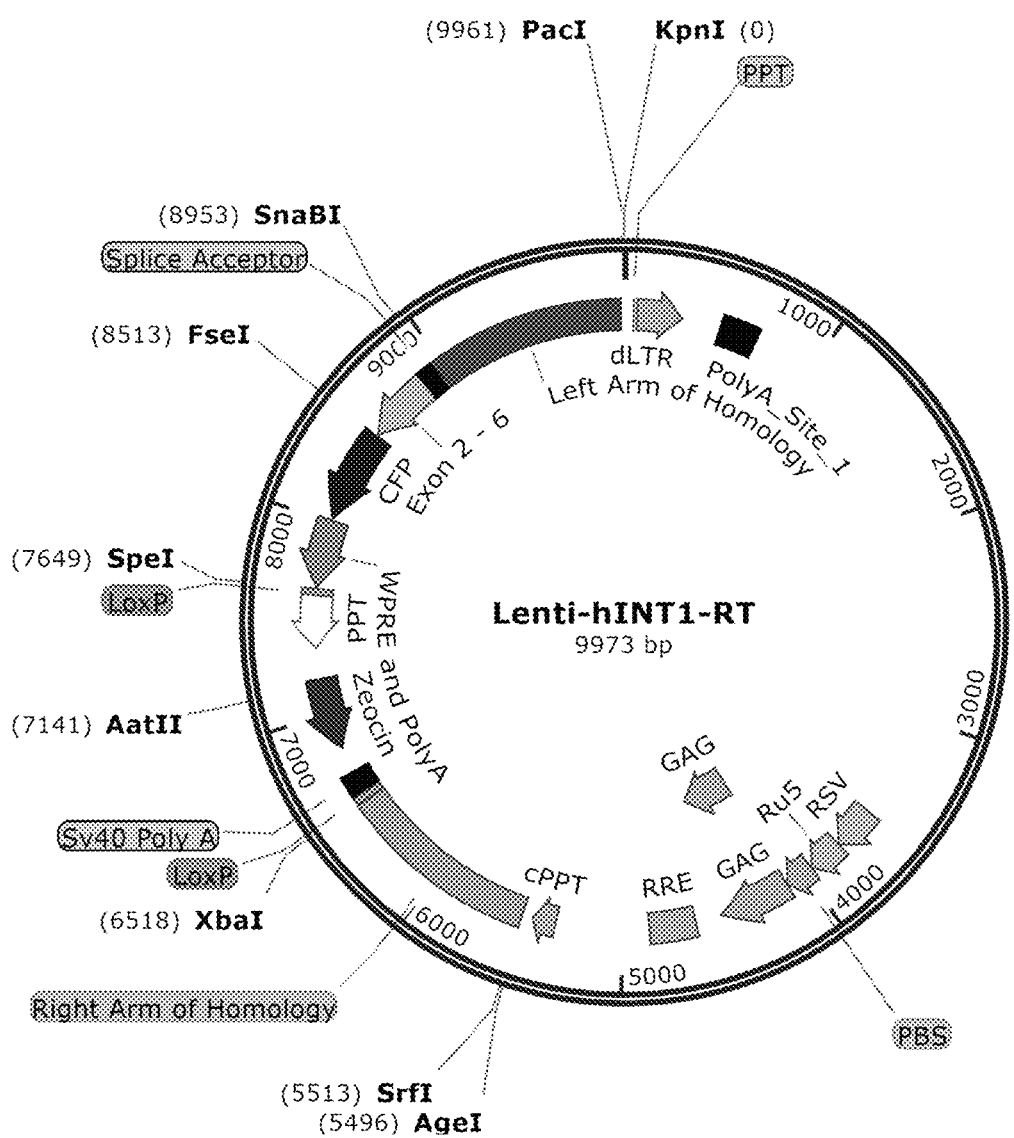

FIG. 7: A schematic of the Lentiviral human DMD intron 1 plasmid repair template. A lentiviral vector encoding the human DMD Intron 1 repair template; notably, the constituents of the human DMD intron 1 plasmid run in reverse orientation to the transcription of the lentiviral plasmid; this is to prevent aberrant splicing from occurring that may be detrimental to viral mRNA transcription and subsequently viral production. This includes the FseI and NotI cloning sites downstream of optimised DMD cDNA exons 2-6, CFP protein and Woodchuck hepatitis virus regulatory element (WPRE). In addition the upstream and downstream 1 kb arms of homology isogenic to the genomic sequence adjacent to the guide sites in intron 1 and the floxed zeocin cassette are also present.

EXAMPLES

This work was carried out to assess the expression of recombinant dystrophin protein resulting from both native and sequence optimised cDNA encoding full-length dystrophin.

Materials & Methods

Materials and Methods for characterisation of expression differences of full-length native and sequence optimised dystrophin:

Viafect Transient Transfection

Materials

Viafect Transient Transfection Reagent (Promega)
Serum Free Dulbecco's Modified Eagle's Medium (DMEM) (Gibco)
Hek293T Cells (ATCC)
Six Well Plate (Corning)
Sterile Eppendorfs (Corning)

Method

Hek293T cells were seeded at a density of $5\times10^5$ at Day 0 to attain 70-80% confluency 24 hours post seeding. The growth media was carefully changed 1 hour prior to transient transfection. During this time, master mix was produced comprising: 20 μl of viafect reagent (Promega) and 4 μg of native or sequence optimised dystrophin made to a 200 μl volume per well using serum free DMEM (Gibco). Importantly, the transfection reagent (μl):DNA mass (μg) was maintained at a 5:1 ratio, when the mastermix was produced it was adjusted to include an extra half a well to account for pipetting error and all transient transfections were undertaken in a six well plate (Corning).

In the production of a mastermix, a calculated volume of serum free DMEM at room temperature was pipetted into a sterile eppendorf. Then 4 μg of DNA was added and the DNA-DMEM suspension agitated. This was incubated at room temperature for 5 minutes as per the manufacture's protocol. Then a defined volume of Viafect transfection reagent was added drop-wise with continual agitation of the suspension and incubated at room temperature for 15 minutes. Post incubation, the transient transfection mixture was added to the well in a dropwise circular motion to ensure maximum cell coverage. Notably, this was also performed alongside a 'Mock' condition in which cells were incubated in the presence of Viafect and DMEM in the absence of DNA, as a control.

Due to the non-toxic nature of Viafect transfection reagent a media change was not necessitated post transfection. Cells were incubated for 72 hours prior to harvesting for total protein lysate.

Protein Extraction and Quantification:

Materials
Sterile PBS: 1 PBS Tablet (Gibco) dissolved in 500 ml of ddH20. This was either autoclaved or filtered with a 0.22 μM filter, with Class II Lamina flow hood.
PAPBNI Buffer: NaCl 0.15M, HEPES 0.05M, NP-40.1%, Sodium Deoxycholate (SOC) 0.5%, SDS 0.10%, EDTA 0.01M, Protease Inhibitor tablet 1 in 50 ml (Roche). This was aliquoted into 5 mls, and stored at −20.
Cells Scrappers (Invitrogen)
Eppendorfs
Benchtop Microcentrifuge
DC Assay Protein kit: Reagent A, S and B (BioRad).
2 μg BSA Standard (Invitrogen)
96 Well plate (Corning)
96 Well plate reader (Genbank)

Protein Extraction:

Post 72 hour incubation, growth media was aspirated, cells were washed with 500 μl ice cold PBS and 100 μl PABPN1 RIPA Buffer added. The cells were then scrapped down to the bottom of the well, with the plate held at a 45° angle, before being incubated at 4° C. on ice for 5 minutes. The samples were then transferred to pre-chilled and labelled eppendorfs, prior to being vortexed every 30 seconds for a further 15 minutes. The resultant protein lysates were then centrifuged at 13,000 rpm for 15 minutes, in a benchtop microcentrifuge to allow cell debris to pellet. The supernatant was then transferred to a fresh pre-chilled and labelled 0.5 ml screw top tube, and stored at −20° C.

Protein Quantification:

A defined dilution series of BSA in the protein extraction PABPN1 Buffer is prepared providing concentrations ranging from 0-2 μg of BSA respectively. As shown below:

| Conc (μg) | 2 | 1.8 | 1.5 | 1.2 | 1 | 0.8 | 0.6 | 0.4 | 0.2 | 0 |
|---|---|---|---|---|---|---|---|---|---|---|
| RIPA buffer | 0 | 4 | 10 | 16 | 20 | 24 | 28 | 32 | 36 | 40 |
| BSA | 40 | 36 | 30 | 24 | 20 | 16 | 12 | 8 | 4 | 0 |

These protein standards were loaded at a volume of 0.5 μl, alongside extracted protein samples at a volume of 5 μl in a 96 well plate. All samples were loaded in triplicate to assert the accuracy/ensure reliability of the resulting absorption readings obtained.

In the fume hood: Reagent A+S (1 ml of A to 20 μl of S) was added at volume of 25 μl to each of the samples from a low to high concentration wherever possible; this being a precautionary measure to prevent contamination. Subsequently, 200 μl of Reagent B is applied and the resultant mixture is agitated and incubated for 15 minutes at room temperature. A colorimetric analysis is undertaken at 750 nm using the (Gen) 96 well plate reader. The absorption readings were then, used to calculate an average protein concentration of the three samples from the standard curve.

Western Blotting

Materials

NuPage 10× Reducing Agent (ThermoFischer)
NuPage 4× Loading Dye Sample (ThermoFischer)
NuPage 3-8% Tris Acetate precast gradient gels (ThermoFischer)
NuPage Antioxidant (ThermoFischer)
Prestained HiMark Ladder (Life technologies)
NuPage 3-8% Tris Acetate Running Buffer (ThermoFischer)
NuPage 20× Transfer Buffer (ThermoFischer)
Absolute Methanol (VWR)
I-Cell Blot Tank (Thermo Fischer)
0.45 μM Nitrocellulose membrane (GE Healthcare)
Ponceau Stain (ThermoFischer)
Filter paper
Marvel Milk Powder
Tween 20 Detergent (Sigma)
ECL solution 1 and 2 (Promega)
Amersham Hyperfilm 18 cm×24 cm (GE Heatlhcare)
Odyssey SA (Licor)

Antibodies

Primary Antibodies

| Antibody name | Raised in | Dilution Used | Binds to |
|---|---|---|---|
| 6C5 (Dr. Glenn Morris) | Mouse | 1 in 100 | 17.a.a C-Terminal |
| Mannex 1011C (Dr. Glenn Morris) | Mouse | 1 in 100 | Hinge/Spectrin repeats (Exon 10-11) |
| Tubulin (Abcam 40774) | Rabbit | 1 in 2500 | Alpha Tubulin Subunit |

Secondary Antibodies

| Antibody name | Dilution Used |
|---|---|
| Goat α Mouse (Green Fluorescence) (LI-COR) | 1 in 10000 |
| Donkey α Rabbit (Red Fluorescence) (LI-COR) | 1 in 10000 |

Sample Preparation

Samples of total protein lysate were produced in a 4× master mix, this was to allow repetitions with antibodies if required. Typically a 4× 40 ul master stock would contain 200 μg total protein. Samples were then prepared in a 1.5 ml screw top tube with: 4 μl Reducing Agent, 10 μl of Loading Sample Dye and the remaining volume is supplemented with ddH20. The samples were prepared alongside a positive control, either dystrophin extracted from muscle or from a previous positive transfection. Then denatured by heating to 70° C. for 10 minutes.

Gel Preparation and Electrophoresis

A 3-8% Tris-Acetate precast gradient gel (ThermoFischer) was used to resolve the full length dystrophin protein. In preparation of the gel, the comb was removed and wells washed with ddH20. In addition, a white adhesive strip sealing the foot of the gel was removed. Gels were then placed in the I-Cell Blot tanks vertically. Then a 10 μl aliquot of the 4× master stock of each protein sample was loaded alongside, a pre-stained Hi-Mark ladder (Life Technologies). The surrounding tank was filled approximately 1 cm from the top, with 1× 3-8% Tris-Acetate buffer and 500 μl of antioxidant was applied immediately prior to the initiation of electrophoresis. The gel was run for approximately 1 hour and 15 minutes at 150V, in accordance with the Nupage technical guide. The blue loading dye reaching the 'foot' of the gel and the ladder separation were parameters by which sufficient separation was assessed. During this time blotting pads were soaked in 1× transfer buffer: supplemented with 10% methanol and 1 ml antioxidant. Filter paper and 0.45 μM nitrocellulose membranes were cut to correct size for the transfer.

Electro-Transfer to Nitrocellulose Membrane.

Upon suitable separation of the ladder and by extension the proteins; the Nupage Electro-transfer cassette was prepared in accordance with the protocol (see NuPage Technical guide 2013).

Once pre-soaked blotting pads were applied to the bottom of the electro-transfer cassette, the 3-8% Tris acetate gels cases were 'cracked' open to liberate the polyacrylamide gels. The top of the gel, above the top band of the Hi-Mark ladder was removed and disregarded. The remainder of the gel was floated, using the buffer, to be situated above filter paper, lifted out of the transfer buffer and placed to the transfer cassette. Once performed, the 0.45 μm nitrocellulose membrane was submersed in buffer and placed on top. This was then rolled across the surface of the gel using a plastic roller to ensure tight contact throughout. A filter paper and a blotting pad placed on top. The whole cassette was kept wet during this time. If a second gel was present then the process was repeated. When completed this was placed in the I-Cell tank. The top of the electro-transfer cassette was refilled with 1× transfer buffer and the surrounding area filled with cold ddH20. The proteins were then transferred for 2 hours at 30V.

Post-Transfer Checks and Blocking

Following the two hour transfer, the membrane was stained with 1× Ponceau. This stains all proteins across the lanes and is used to ensure that the transfer was complete and successful. The stain was then washed off with 0.1% PBS-T, washing at 5 minute intervals until no stain was visible.

The nitrocellulose membrane was then blocked with 5% Marvel milk in 0.1% PBS-T for 1 hour at room temperature, to prevent non-specific binding. Once the membrane was blocked, the membrane was cut in half between the 55 and 71 kDa HiMark Ladder bands. The top piece of 0.45 μM nitrocellulose was incubated at 4° overnight in a 1 in 100 dilution of 6C5 or MannEx10-11c and the bottom a 1 in 2500 dilution of Rabbit Anti-tubulin.

Visualisation of the Nitrocellulose Membrane Using the Odyssey

Following overnight incubation with primary antibodies, 4 washes in 0.1% PBS-T was undertaken for 5 minutes. The secondary antibodies, which are conjugated to a fluorescent label were diluted to 1 in 10,000. The nitrocellulose membrane was then incubated for a further hour, prior to the repetition of 4 washes for 5 minutes in 0.1% PBS-T. This was then scanned at 700 nm and 800 nm channels respectively, using the Odyssey SA machine (Li-Cor). Dystrophin would be present within the 800 nm channel and the α-tubulin present within the 700 nm channel.

Quantification of Dystrophin

Software

Image Studios Version 4 (Li-Cor)

Methods

The nitrocellulose membrane was then visualised with Image Studios Version 4. Bands were automatically identified using the software, and adjusted to be tight to the band in question in individual 800 nm and 700 nm channels. User defined noise values were subtracted away from the band in question and used to attain intensity values, for both dystrophin (800 nm) and α-tubulin (700 nm). The values were normalised to tubulin:

$$\frac{\text{Dystrophin Fluorescence Intensity}}{\alpha - \text{Tubulin Fluorescence Intensity}} = \text{Normalised Values}$$

This was performed for each lane and the native and optimised dystrophin (n=5) and a mean value was attained. Once mean values were attained the Sequence optimised dys/tub ratio was normalised to the native dys/tub, to establish a fold difference in expression.

Results

Initial Assessment of Dystrophin Expression from Native and Optimised, GFP Tethered Dystrophin Constructs:

Initially, a visual indication of whether sequence optimisation improves transcription and subsequently synthesis of recombinant dystrophin protein was sought. In pursuit of this plasmids containing native and optimised full-length dystrophin cDNA (SEQ ID NO: 1) directly tethered to eGFP were transiently transfected into Hek293T culture. Plasmids were driven by the Cytomegalovirus (CMV) promoter, a strong viral promoter to ensure higher levels of protein expression. The direct tethering of eGFP to dystrophin enables fluorescence to be used as an indicator of dystrophin expression; particularly, as the stoichiometry of eGFP:dystrophin is equivalent in the resultant fusion protein.

Both full-length native and optimised dystrophin plasmids were transfected at a 4 µg dose to Hek293T using a 5:1 transfection reagent:DNA ratio. Cultures were then subject to microscopy imaging at 24, 48 and 72 hours post transfection; the latest time point in this series, being reflective of the time taken for dystrophin protein to accumulate, to optimal levels for detection by western blotting.

Figure 1:
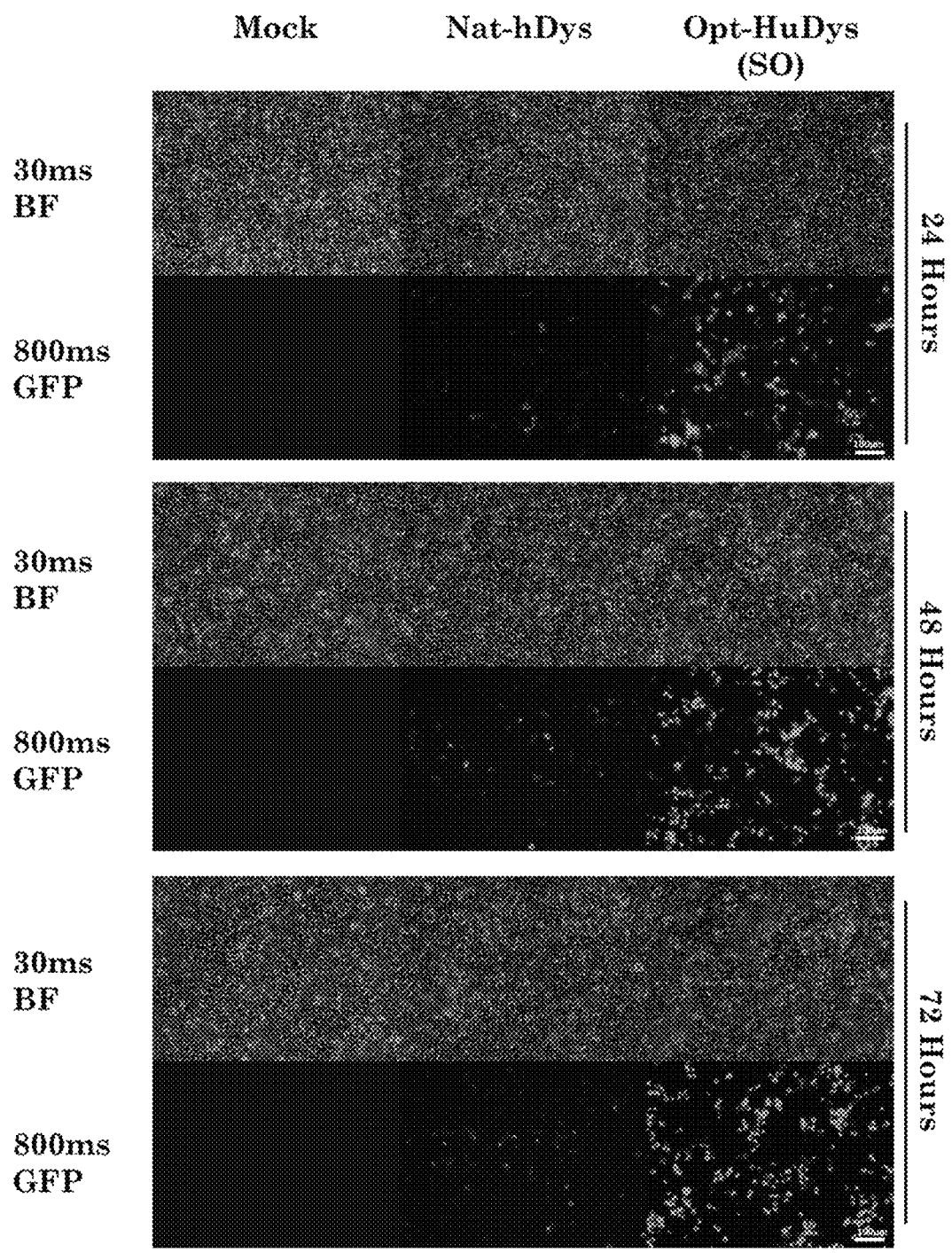
FIG. 1: Visual demonstration that sequence optimisation of cDNA improves recombinant protein expression as demonstrated by using constructs encoding native and optimised, full-length dystrophin tethered to eGFP. Hek293T cells transfected with native and sequence optimised full-length dystrophin-eGFP constructs, Nat-hDys and Opt-HuDys (SO) respectively. Transient transfections were undertaken at 4 µg with a 5:1 viafect reagent:DNA ratio. Subsequent GFP expression was imaged at sequential time points of 24, 48 and 72 hours with the Zeiss microscope at 10× magnification and 30 ms BF and 800 ms GFP channel exposures. A noticeable accumulation of green fluorescence can be seen in sequential time points for both constructs; in addition a difference in fluorescence intensity is seen between native and optimised dystrophin encoding constructs.

There was an apparent difference in green fluorescence, observed between native and optimised cultures post-transfection, across all time points examined. Initially, the number of GFP positive cells in the culture, indicated successful transfection of both native and optimised constructs. Moreover, the intensity of fluorescence appears to increase from 24-72 hour time points irrespective of optimisation; likely attributable to the accumulation of dystrophin-eGFP transcript and subsequent protein synthesis. However, there was a striking increase in fluorescence intensity, observed in the optimised dystrophin culture relative to the native, at all time points examined (FIG. 1). This was suggested to be due to the sequence optimisation of the plasmid. The proposed implication being that the optimised construct enhances transcriptional efficiency and subsequently dystrophin-eGFP protein synthesis.

Quantifying the Difference in Expression of Native and Optimised Dystrophin Constructs Driven by a CMV Promoter:

The increased fluorescent intensity observed, prompted direct assessments of dystrophin protein expression for both CMV driven Nat-hDys and Opt-HuDys (SO) constructs. It was resolved that constructs without the GFP tag should be used in this examination. Transient transfections of plasmids were repeated at 4 µg utilising the 5:1 viafect transfection reagent:DNA ratio previously described. Cultures were incubated for 72 hours post transfection and lysed for total protein; this being in line with optimal accumulation of dystrophin protein. The samples were subsequently quantified and screened with two dystrophin antibodies: The 6c5 antibody, which binds to the carboxyl C-terminus of the dystrophin protein and the MannEx1011c, which binds to a dystrophin protein epitope, encoded between exons 10 and 11. This was performed prior to subsequent visualisation and quantification against an alpha-tubulin loading control using the Odyssey Licor system.

Figure 2:
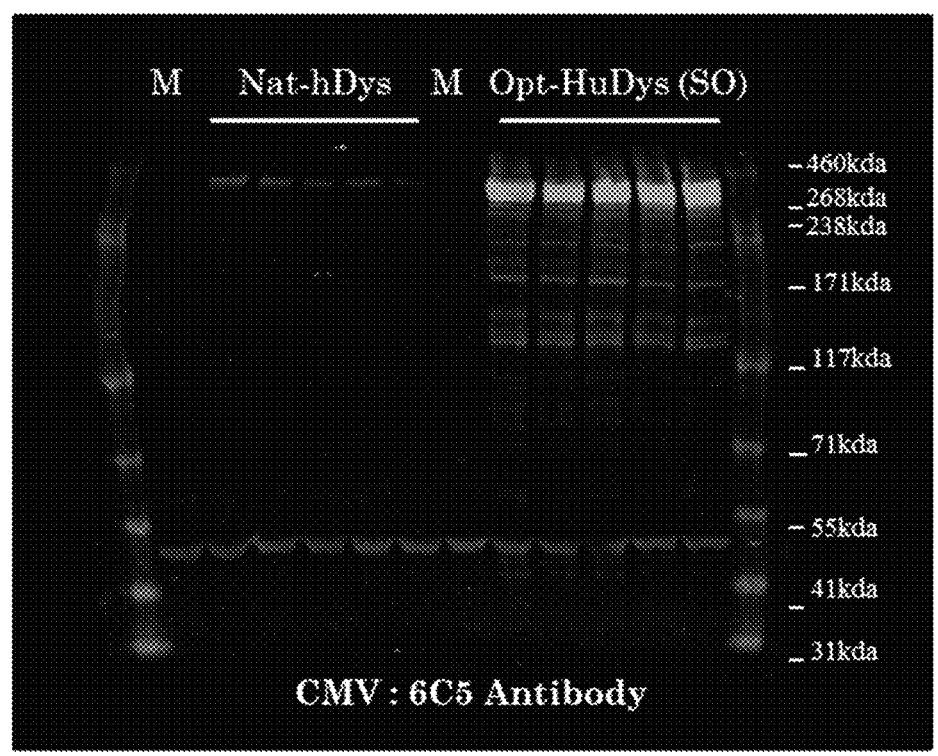
FIG. 2: Optimisation of cDNA sequence increases recombinant dystrophin expression. Plasmids expressing native (Nat-hDys) and sequence-optimised dystrophin (Opt-HuDys-SO) cDNAs from the CMV promoter were transfected into HEK293 cells (n=5). After 72 h cultures were harvested and processed for Western blotting (A) 50 µg total protein lysate was analysed with antibodies to dystrophin (6C5) and alpha-tubulin. Dystrophin bands were then quantified relative to the alpha-tubulin loading controls and mean intensity ratios plotted (B: mean±SEM: ***8 $p<0.001$ (unpaired t-test). Sequence optimisation produced a 57-fold increase in expression.
Figure 2:
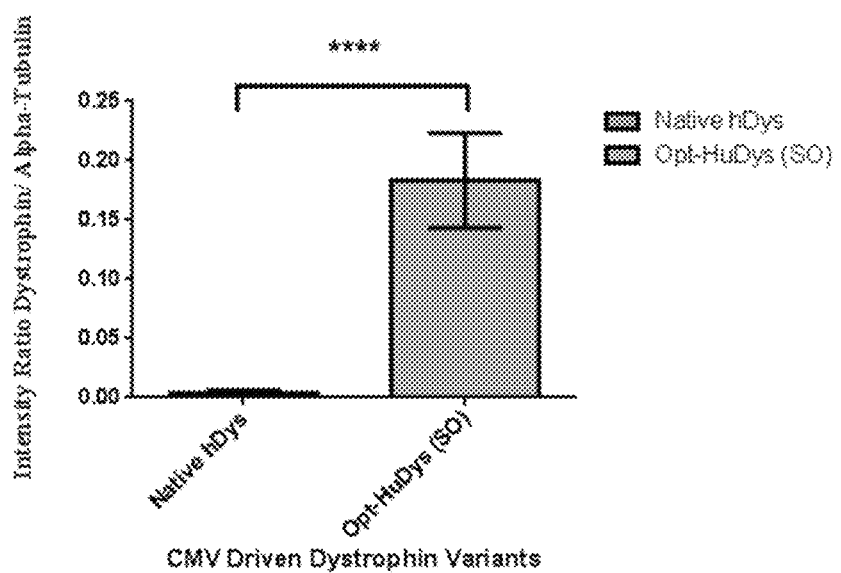
Figure 3:
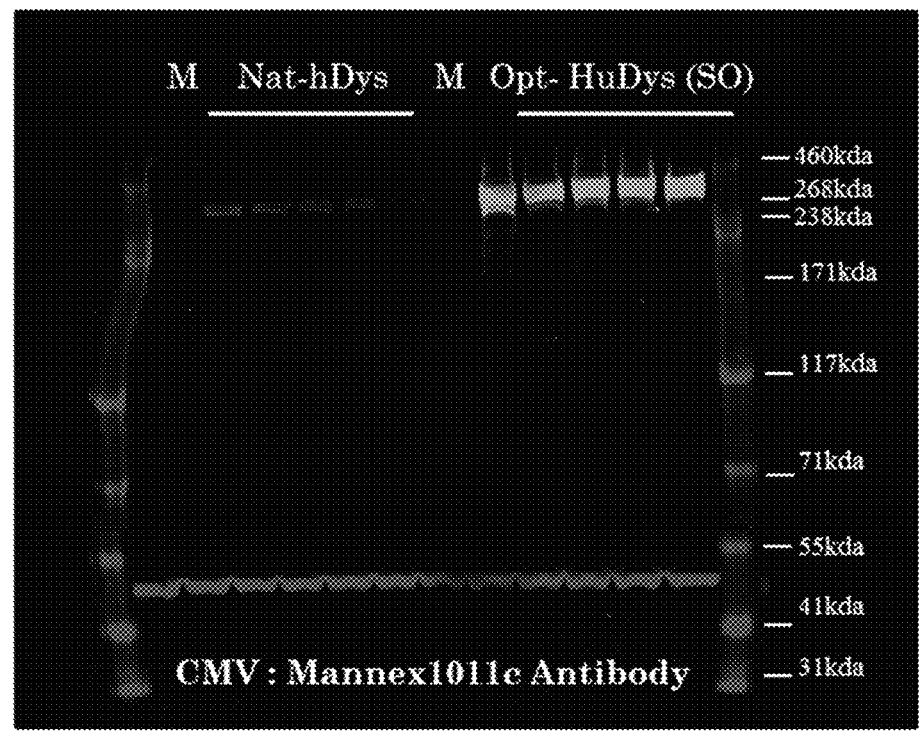
FIG. 3: Optimisation of cDNA sequence increases recombinant dystrophin expression. Plasmids expressing native (Nat-hDys) and sequence-optimised dystrophin (Opt-HuDys-SO) cDNAs from the CMV promoter were transfected into HEK293 cells (n=5). After 72 h cultures were harvested and processed for Western blotting (A) 50 µg total protein lysate was analysed with antibodies to dystrophin (ManEx1011c) and alpha-tubulin. Dystrophin bands were then quantified relative to the alpha-tubulin loading controls and mean intensity ratios plotted (B: mean±SEM: ***$p<0.001$ (unpaired t-test). Sequence optimisation produced a 22-fold increase in expression.
Figure 3:
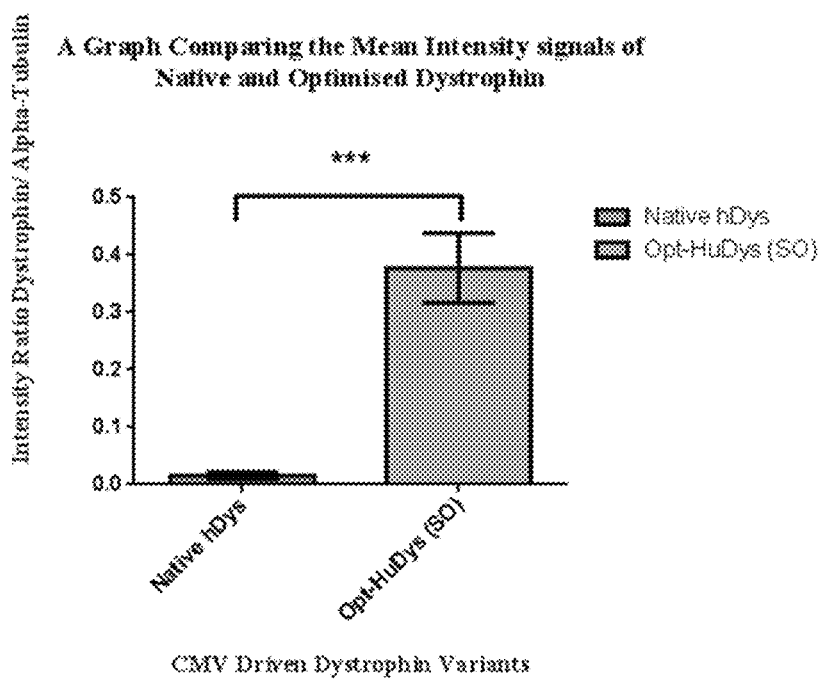

Importantly both constructs Nat-hDys and Opt-HuDys (SO), expressed a 427 kDa protein as determined by a HiMark Nupage Ladder, consistent with full-length dystrophin. This was detected with both the 6C5 and the MannEx1011c antibodies. Congruent with the previous investigation, the sequence optimised construct yielded a larger area band with increased intensity relative to the native. This trend was retained across 5 samples that were transiently transfected (FIG. 2 and FIG. 3). During the quantification, dystrophin fluorescence in the 800 channel was divided by tubulin in the 700 channel and a mean of Opt-HuDys-SO ratios attained were normalised to that of Nat-Dys. This form of analysis indicated a striking 57-fold difference with 6C5 antibody and a 22-fold difference with the MannEx101c antibody. This was deemed statistically significant in both cases giving a p=<0.001 by an unpaired t-test.

Additionally, it should be emphasised that on examination of the western blot an alternative banding pattern between the two antibodies was observed. The 6C5 antibody appeared to produce a characteristic laddering pattern in the Opt-HuDys (SO) construct that was not observed in the case of the Nat-hDys construct. The additional banding seen had moderate intensity comparable to the full-length band. In contrast the Mannex1011c antibody resulted in a singular sharp band for both Nat-hDys and Opt-HuDys (SO) constructs, with few additional bands at low intensity. In the case of the latter, this is likely the result of increasing the brightness to visualise the Nat-hDys bands.

Quantifying the Difference in Expression of Native and Optimised Dystrophin Constructs Driven by a Spc512 Promoter:

In the first series of investigations, CMV driven constructs were used. However, in the context of translational application, a muscle specific promoter would be advantageous in providing expression localised to muscle (Counsell J R et al., Sci Rep. 7:44775 (2017) and Meng, J. et al., Scientific Reports, 6(1), p. 19750 (2016)). In examination of this, Nat-Dys and Opt-Dys-SO constructs driven by the muscle specific Spc512 promoter, were transiently transfected at a 4 µg dose and protein harvested at 72 hours. Protein samples were prepared, subject to western blot and quantified in a manner consistent with the CMV based experiments.

Figure 4:
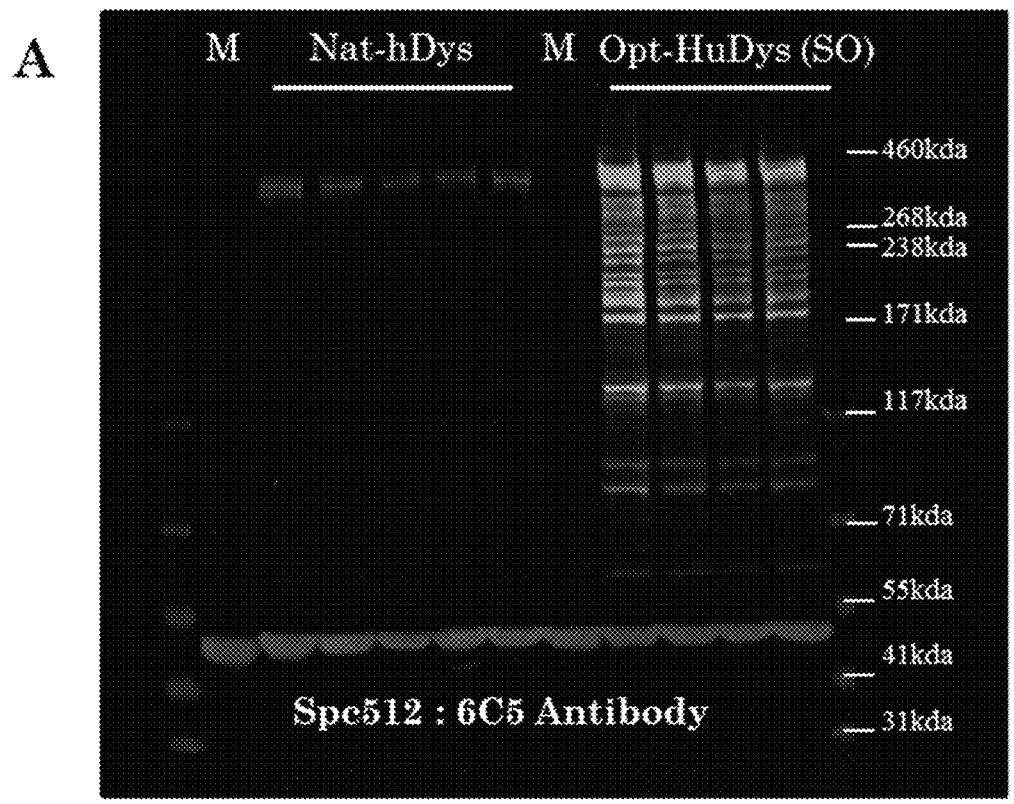
FIG. 4: Optimisation of cDNA sequence increases recombinant dystrophin expression. Plasmids expressing native (Nat-hDys) and sequence-optimised dystrophin (Opt-HuDys-SO) cDNAs from the Spc512 promoter were transfected into HEK293 cells (n=5). After 72 h cultures were harvested and processed for Western blotting (A) 50 µg total protein lysate was analysed with antibodies to dystrophin (6C5) and alpha-tubulin. Dystrophin bands were then quantified relative to the alpha-tubulin loading controls and mean intensity ratios plotted (B: mean±SEM: ***8 $p<0.001$ (unpaired t-test). Sequence optimisation produced a 15-fold increase in expression.
Figure 4:
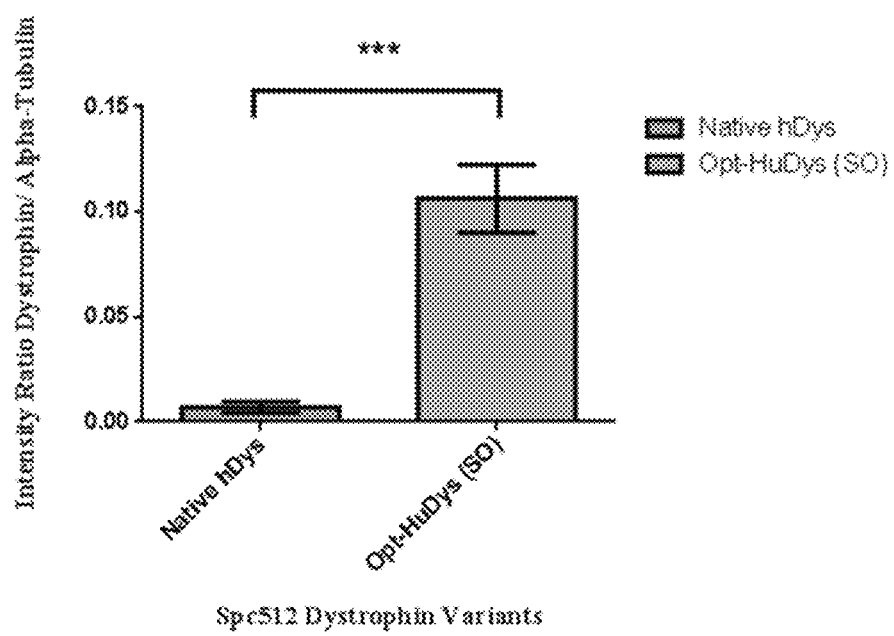
Figure 5:
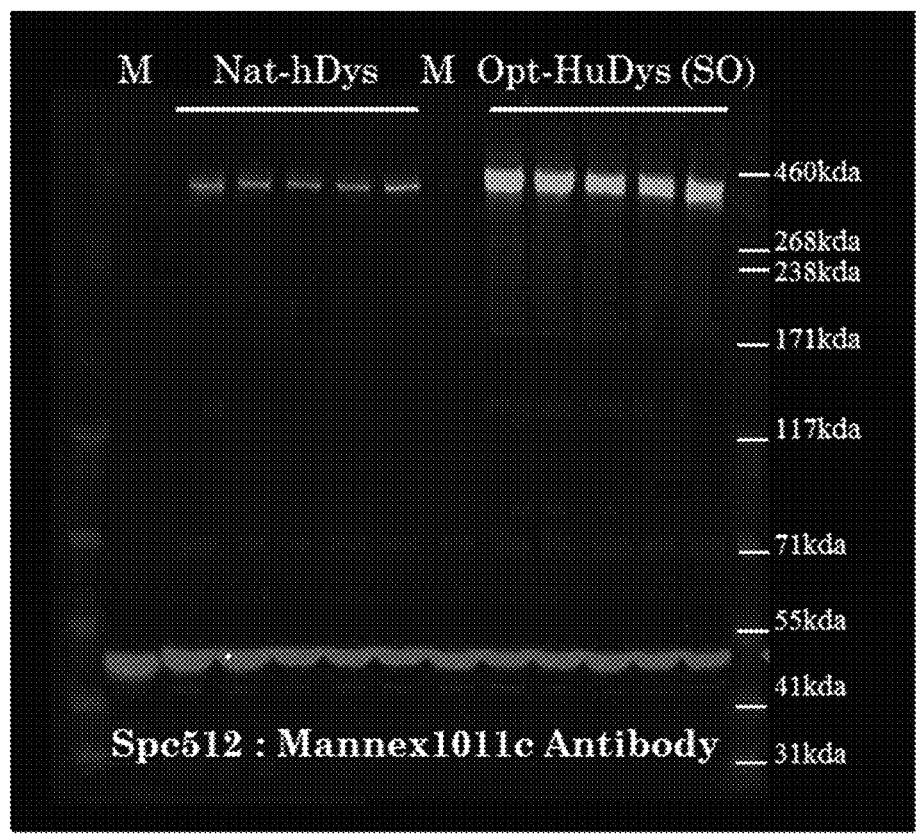
FIG. 5: Optimisation of cDNA sequence increases recombinant dystrophin expression. Plasmids expressing native (Nat-hDys) and sequence-optimised dystrophin (HuDys-CO) cDNAs from the Spc512 promoter were transfected into HEK293 cells (n=5). After 72 h cultures were harvested and processed for Western blotting (A) 50 µg total protein lysate was analysed with antibodies to dystrophin (ManEx1011c) and alpha-tubulin. Dystrophin bands were then quantified relative to the alpha-tubulin loading controls, and mean intensity ratios plotted (B: mean±SEM.
Figure 5:
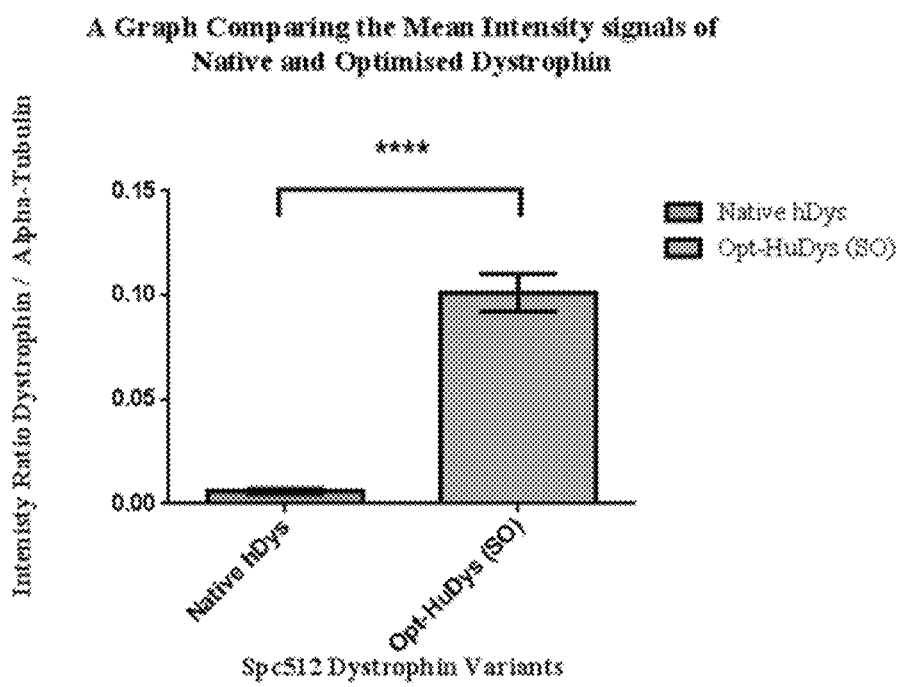

The Opt-Dys-SO construct once again resulted in a protein band of a greater area with an increased fluorescent intensity, relative to Nat-Dys with 6C5 and ManEx1011c antibodies (FIG. 4) and (FIG. 5). In this instance a 15-fold difference and a 17-fold difference were determined respectively. Notably, the difference whilst less prominent than observed with the CMV driven constructs, is still present. Finally, the laddering effect previously observed with the 6C5 antibody, is retained even with the use of an alternative promoter. This finding was somewhat unexpected due to the use of the Spc512 muscle-specific promoter, but was attributed to the Hek293T cell culture enabling 'leaky expression'.

Design of an Exogenous Repair Template:

The exogenous repair template was designed with numerous features to make it optimal for this investigation. Firstly, it included a backbone sequence amenable to the cloning of multiple dystrophin cDNA variants, including the full-length optimised sequence. Secondly, a splice acceptor was appended at the 5' end, in place of a promoter. Moreover, the presence of the 5' splice acceptor would enable the endogenous Dp427m promoter and indeed other full-length promoters to splice to the exogenous repair template. As a consequence, the resultant protein will have the correct spatial and temporal expression patterns. It is hypothesised that this will ameliorate a range of pathogenic disease causing mutations across the DMD gene.

To attain a backbone sequence amenable to the cloning of a variety of dystrophin cDNA transgenes, all unique restriction endonucleases were identified across full-length Opt-HuDys (SO). This served to identify two unique restriction sites. At the 5' end this was FseI, present 30 nucleotides into exon 6 and at the 3' end NotI situated at the terminus of exon 79. Thus a sequence was constructed with: DMD cDNA of exons 2-6 upstream of an FseI site, an intervening cyan fluorescent marker sequence and finally, a NotI site. It was determined that this sequence would enable directional cloning of the sequence optimised dystrophin variant.

In construction of an Exon 2-6 DMD cDNA block, consensus sequences of exons 1-6 of the Dp427m isoform, were aligned against full-length sequence optimised dystrophin cDNA. In this manner exons 1-6 of sequence optimised dystrophin cDNA, was identified. Exon 1, determined as the first 31 nucleotides of the sequence, was subsequently removed (Koenig et al., *Cell,* 50(3), pp. 509-17 (1987)). It was anticipated that these nucleotides would be reconstituted by the endogenous Dp427m promoter, if successful splicing to a delivered dystrophin transgene occurred. To this purpose, exon 2 was flanked at the 5' end with a human β-globin synthetic splice acceptor, and other regulatory sequences to facilitate splicing, including: a polypyrimidine tract and synthetic branch points (Seth et al., *The Journal of biological chemistry,* 283(15), pp. 10058-67 (2008); Popplewell et al., *Human gene therapy,* 24(7), pp. 692-701 (2013)). These sequences were modified to include a silent mutation, to generate a HpaI restriction site and identified as a strong splice acceptor by human splice finder (Desmet et al., *Nucleic acids research,* 37(9), p. e67 (2009)). Thus this splice sequence was selected to facilitate the splicing of the endogenous promoter to the integrated dystrophin transgene. Moreover, the inclusion of the HpaI restriction site would enable this sequence to be replaced with a native sequence with ease should this be required.

The 3' end of this cDNA block, downstream of the NotI site, was also flanked by a sequence indicated to improve transcription in lentiviral vectors; this being a mutated Woodchuck Hepatitis Virus Post-transcriptional regulatory element (mWPRE) fused to a polyA (Ranzani et al., Nat Methods. 10(2):155-61 (2013)).

Between these FseI and NotI sites, a Cyan fluorescent protein (CFP) was encoded. The sequence was modified to remove the initiating methionine and append the first two nucleotides of DMD exon 2. This was undertaken to retain the open reading frame of partial Dys-CFP fusion protein and reduce background fluorescence that may arise from aberrant firing of the methionine. This was anticipated to provide the benefit of a visual blue-fluorescent output, which could be used to indicate Dys-CFP transgene integration and track subsequent enrichment processes. It was anticipated that this would streamline the development of integration methods, in Hek239T and patient myoblast cultures. Moreover, the intervening CFP sequence could be used as a spacer within the DMD intron 1 repair template. The presence of a 491 bp band, removed upon FseI and NotI double digest could be used to indicate successful cleavage of the repair template and facilitate sub-cloning of dystrophin cDNA variants.

Due to the HDR pathway occurring with relatively low efficiency, an antibiotic selection cassette, SV40-Zeocin-PolyA, was placed downstream of the WPRE and PolyA sequences. This encodes the She Ble protein, which when expressed renders the zeocin antibiotic inactive (Hockemeyer et al., *Cell stem cell,* 3(3), pp. 346-353 (2008)). This sequence was modified to include a silent point mutation to remove a FseI site present. This ensured the unique core FseI and NotI sites required for directional sub-cloning of dystrophin variants was retained.

The zeocin selection cassette was resolved upon, as during immortalisation process of patient myoblasts, harbouring the deletion of exons 45-52 (Δ45-52); they were rendered resistant to puromycin and neomycin antibiotics (Mamchaoui K. et al., *Skeletal muscle,* 1, p. 34 (2011)). Importantly, the cassette was floxed with LoxP sites that can conditionally remove intermediate sequences, in the presence of Cre-recombinase. Inclusion of the sequences of the LoxP sites was necessitated as post-enrichment of cells with successful integration; continued expression of the She Ble protein is undesirable. This is due to concerns that if cellular material is used to treat patients, in an ex-vivo engraftment manner they may acquire antibiotic resistance, which would have implications on their endogenous flora (Marie et al., *The Journal of Gene Medicine,* 12(4), pp. 323-332 (2010)).

Once the sequences of all constituents were obtained, they were flanked with 1 kb arms of homology. These were derived from human DMD Intron 1 consensus sequence from NCBI. The 1 kb arms initiated 6 nucleotides upstream of guide 3 and downstream of guide 4; these being the most upstream and downstream of the CRISPR guides identified. The arms of homology were designed in this manner, as a single guide with the highest efficacy had not yet been identified. As a direct consequence of this, no guide sequences were encoded within the exogenous repair template. Thus circumventing the risk that the repair template may be cleaved or indeed dystrophin variants re-targeted upon integration into the genome, by the Cas9 system.

Once a full sequence of the human DMD intron 1 repair template was compiled, it was assessed in parallel with dystrophin variants and the ISceit-Lentiviral vector for common for non-cutters. The list of common non-cutters were examined for compatibility in a double digest setting and used to flank all components of the exogenous repair template. This sequence was used and the repair template in a Puc57 backbone was synthesised (FIG. 6). Finally, the sequence was inserted in reverse orientation into the ISciet lentiviral backbone; this was performed to maintain the viral mRNA structure and prevent aberrant splicing or termination occurring (FIG. 7).

Sub-Cloning the Optimised Full-Length Dystrophin cDNA into the Puc57 Intron 1 Exogenous Repair Template:

Following the synthesis of the Intron 1 exogenous repair template, focus was shifted to the sub-cloning of the optimised full-length dystrophin from Exon 6 to exon 79 between the FseI and NotI endonuclease restriction sites. To this purpose, the optimised full-length dystrophin was subject to a series of diagnostic digests to assert the identity of the construct. Once assured the construct digested in a manner consistent with that anticipated; both the destination vector Puc57-hINT1-RT and the optimised full-length dystrophin plasmids were subject to double digest with FseI and NotI restriction endonucleases. In the case of the destination vector the double digest served to remove the CFP marker and leave a 6638 bps backbone. Whereas in the case of the optimised full-length dystrophin it enabled the cDNA insert of interest to be liberated. Samples were resolved by electrophoresis and subjected to overnight ligation, post gel purification. Subsequent ligation mixtures of insert and destination vector and a vector control, containing only digested backbone, were then subjected to standard heat shock transformation. The *E. coli* suspension was allowed to recover and plated onto ampicillin plates for an overnight incubation at 30° C. The vector control yielded no colonies, indicating that no self-ligation had occurred, likely attributable to the incompatible DNA termini resulting from the double digest. In contrast, the ligation mixtures yielded a high number of single colonies that could be picked and characterised. These results taken together serve to indicate that the optimised full-length dystrophin fragment from exon 6-79 was likely ligated into the destination vector backbone.

In an attempt to assess whether ligation was successful a colony PCR was undertaken. The primer pairs were designed for the colony PCR, so the forward primer was present within the Exon 2-6 region of the Puc57-hINT1-RT backbone upstream of the FseI cleavage site; whereas the reverse primer would only be present if the optimised full-length dystrophin insert was ligated. Thus the resultant amplicon was only anticipated to occur in instances where the optimised full-length dystrophin transgene had been successfully inserted into the Puc57-hINT1-RT destination vector. Amplification of the Spc512-HuDys (SO) plasmid was used as a positive control, the Puc57-hINT1-RT destination vector pre-digest and ligation served as a negative control.

The first 4 colonies from the colony PCR series were selected, grown as a starter culture, mini-prepped and subject to restriction digest. This was to further confirm presence and identity of the optimised full-length dystrophin transgene insert. Initially, the FseI and NotI double digest were performed on putative Puc57-hINT1-HuDys-RT constructs, alongside the parental Spc512-HuDys SO plasmid, which provided the insert. All four colonies gave the anticipated digest profile, alongside the Spc512-HuDys (SO) control plasmid.

Additionally, a diagnostic digest using the ScaI restriction endonuclease was undertaken. This produces distinct banding patterns for the parental Spc512-HuDys (SO) and the Pu57-hINT-HuDys-RT. Once again the four colonies gave the anticipated digest profiles, consistent with the optimised full-length dystrophin being inserted into the Puc57-hINT-RT. The above screens indicate a repair template carrying the optimised full-length dystrophin exons 2-79 and an independent selection cassette, all flanked by arms of homology was produced.

Discussion

Sequence Optimised Dystrophin cDNA:

Sequence optimisation of full-length dystrophin cDNA was shown to enhance protein expression relative to native controls. This was established by microscopy imaging and western blotting. Both studies utilised plasmid constructs under the control of a CMV promoter, with the first investigation using dystrophin variants directly tethered to eGFP. Importantly, in the case of full-length dystrophin, a 22-fold difference in protein expression was observed between native and optimised constructs. This large increase in protein expression from optimised cDNA from both experiments was striking.

The investigation was then extended to include optimised full-length dystrophin cDNA under the control of the Spc512 muscle restrictive promoter (Li et al., Nat Biotechnol. 17(3):241-5 (1999); Athanasopoulos et al., Methods Mol Biol. 709:21-37 (2011)). This was performed to examine whether the expression of Spc512 driven constructs could be compared in Hek293T cell culture. Importantly, the Spc512 promoter enabled full-length dystrophin expression in Hek293T cell culture; this is speculated to be due to this cell-line facilitating leaky expression of this promoter. Interestingly, native and optimised full-length dystrophin cDNA produced a varying fold difference in protein expression, when constructs were driven by the CMV and Spc512; being 22-fold and 15-17 fold respectively. This effect is attributed to two main parameters: the first being the relative strengths of the viral CMV and the muscle restrictive Spc512 promoters. Secondly, it was speculated that the expression of the full-length dystrophin cDNA may be reduced with the Spc512 promoter, due to its restrictive expression pattern.

The observations from both CMV and Spc512 studies together, could hold important implications for clinical translation. Numerous studies have provided an insight into the amount of dystrophin protein expression required relative to wild-type endogenous levels to ameliorate dystrophic pathology. Variable estimates have arisen, likely attributable to the nature of investigation from which estimates were derived and how dystrophin levels were quantified. Dystrophin expression of: 30% in BMD patients, 15% following antisense therapy in mice and finally, 20% in transgenic mice, were all shown to confer therapeutic benefit. Whilst estimates of therapeutic dystrophin expression vary between 15-30% among these investigations; they agree a uniform dystrophin expression across the majority of myofibres, as opposed to a sporadic distribution provides greater functional improvement. In addition, they indicate that the level of dystrophin correction required to be therapeutic, will be influenced by the muscle pathology and disease progression of the patient seeking treatment. The striking increase in protein expression observed, with the use of sequence optimised cDNA encoding full-length dystrophin, and relative to its native counter-part could facilitate the attainment of such expression thresholds. By extension of this it is speculated they could greatly improve clinical outcomes and functional improvements observed in clinical trials.

The striking fold differences in protein expression observed between native and optimised constructs necessitate the examination of the potential effects of supra-physiological levels of dystrophin proteins. Importantly, others have demonstrated that overexpression of full-length dystrophin, of up to 50-fold higher than endogenous levels, was well tolerated (Chamberlain, Soc Gen Physiol Ser. 52:19-29 (1997); Phelps S F, Hum Mol Genet. 4(8):1251-8 (1995); Wells D J, Hum Mol Genet. 4(8):1245-50 (1995)). This level was shown to ameliorate dystrophic pathology with the absence of any detrimental effects.

Design of an Exogenous Repair Template:

The improved protein expression resulting from sequence optimised full-length dystrophin cDNA served to influence exogenous repair template design. This prompted the generation of a backbone that would enable the directional sub-cloning of sequence optimised full-length dystrophin cDNA, allowing the exogenous repair template to be trialed in integration experiments.

The exogenous repair template was designed to facilitate a Homology Directed Repair (HDR) outcome, at the human DMD intron 1 locus. It was designed with 1 kb arms of homology isogenic to the human genome, directly upstream and downstream of the region of homology identified. This length of isogenic sequence is deemed optimal for successful exploitation of HDR pathways. Extension of homology arms beyond this size only result in marginal increases of transgene integration. In addition, the repair template also includes a floxed zeocin cassette, to facilitate positive selection processes (Mulsant et al., Somat Cell Mol Genet. 14(3):243-52 (1988); Seth et al., *The Journal of biological chemistry*, 283(15), pp. 10058-67 (2008)). This would enable enrichment of corrected cells, which is important due to the low efficiency of the HDR process.

Importantly, as scientists' understanding of the DNA damage response (DDR) continues to evolve, so too does the manner in which DNA repair pathways are exploited to facilitate the integration of genetic material. Recent investigations have used NHEJ-DNA repair pathways to introduce genetic material (Maresca et al., Genome Res. 23(3): 539-46 (2013); Suzuki et al., Nature. 540(7631):144-149 (2016)). This strategy is reliant upon genomic target sites of the endonuclease TALEN or CRISPR, being encoded in reverse orientation directly adjacent to the transgene for which integration is desirable. The resultant in-situ cleavage of genome and exogenous repair template, facilitates the integration of the transgene independently of the HDR pathway (Suzuki et al., Nature. 540(7631):144-149 (2016)). Importantly, the exogenous repair template in this investigation was designed so components were flanked with endonuclease restriction sites. Thus it could be easily customised to facilitate exploration of such strategies with dystrophin cDNA.

CONCLUSIONS

A novel exogenous repair template was designed with restriction sites enabling the sub-cloning of full-length sequence optimised dystrophin cDNA. This design was founded upon the demonstration that sequence optimisation enhanced recombinant dystrophin protein expression. It was designed with 1 Kb arms of homology isogenic to sequences upstream and downstream of the CRISPR MIT guide designs, identified within human DMD intron 1. Furthermore, it encodes a floxed zeocin cassette to facilitate positive selection during HDR investigations.

SEQUENCES

SEQ ID NO. 1 is a codon optimised full-length dystrophin cDNA including a 3 bp "stop" codon (nucleotides 11,059-11,061).

SEQ ID NO. 2 is the amino acid sequence of the human native dystrophin protein.

SEQ ID NO. 3 is a codon optimised full-length dystrophin cDNA (nucleotides 7-11,064) including a 6 bp optimised Kozak sequence (nucleotides 1-6) and a 3 bp "stop" codon (nucleotides 11,065-11,067).

The invention claimed is:

1. A method of treating muscular dystrophy, the method comprising administering a therapeutically effective amount of a nucleic acid molecule encoding a functional dystrophin protein to a patient suffering from a muscular dystrophy, wherein the nucleic acid molecule comprises a first nucleotide sequence that has at least 94% identity to the sequence of SEQ ID NO: 1.

2. The method of claim 1, wherein the first nucleotide sequence is about 11,025 to about 11,085 nucleotides in length.

3. The method of claim 1, wherein nucleic acid molecule comprises at least exons 2 to 79 of a nucleotide sequence encoding a functional dystrophin protein.

4. The method of claim 1, wherein the first nucleotide sequence has at least 96% identity to the sequence of SEQ ID NO: 1.

5. The method of claim 1, wherein the first nucleotide sequence has at least 97% identity to the sequence of SEQ ID NO: 1.

6. The method of claim 1, wherein the first nucleotide sequence has at least 98% identity to the sequence of SEQ ID NO: 1.

7. The method of claim 1, wherein the first nucleotide sequence has at least 99% identity to the sequence of SEQ ID NO: 1.

8. The method of claim 1, wherein the first nucleotide sequence has the sequence of SEQ ID NO: 1.

9. The method of claim 1, wherein the muscular dystrophy is selected from the group consisting of Duchenne muscular dystrophy (DMD), Becker muscular dystrophy (BMD) and cardiomyopathy.

10. The method of claim 1, wherein the muscular dystrophy is Duchenne muscular dystrophy (DMD).

11. The method of claim 1, wherein the nucleic acid molecule further comprises a second nucleotide sequence, wherein the second nucleotide sequence encodes a protein or peptide that aids in expression of the first nucleotide sequence.

12. The method of claim 1, wherein the nucleic acid molecule is DNA or RNA.

13. The method of claim 12, wherein the nucleic acid molecule is DNA.

14. The method of claim 1, wherein the nucleic acid molecule comprises at least exons 10 to 79 of a nucleotide sequence encoding a functional dystrophin protein.

15. The method of claim 1, wherein the nucleic acid molecule comprises at least exons 45 to 79 of a nucleotide sequence encoding a functional dystrophin protein.

16. The method of claim 1, wherein nucleic acid molecule comprises at least exons 53 to 79 of a nucleotide sequence encoding a functional dystrophin protein.

17. A host cell comprising a nucleic acid molecule comprising a first nucleotide sequence encoding a functional dystrophin protein, wherein the first nucleotide sequence has at least 94% identity to the sequence of SEQ ID NO: 1.

18. The host cell of claim 17, wherein the first nucleotide sequence encoding the functional dystrophin protein is about 11,025 to about 11,085 nucleotides in length.

19. The host cell of claim 17, wherein nucleic acid molecule comprises at least exons 2 to 79 encoding a functional dystrophin protein.

20. The host cell of claim 17, wherein the first nucleotide sequence has at least 95% identity to the sequence of SEQ ID NO: 1.

21. The host cell of claim 17, wherein the first nucleotide sequence has at least 96% identity to the sequence of SEQ ID NO: 1.

22. The host cell of claim 17, wherein the first nucleotide sequence has at least 97% identity to the sequence of SEQ ID NO: 1.

23. The host cell of claim 17, wherein the first nucleotide sequence has at least 98% identity to the sequence of SEQ ID NO: 1.

24. The host cell of claim 17, wherein the first nucleotide sequence has at least 99% identity to the sequence of SEQ ID NO: 1.

25. The host cell of claim 17, wherein the first nucleotide sequence has the sequence of SEQ ID NO: 1.

26. The method of claim 1, wherein the first nucleotide sequence has at least 95% identity to the sequence of SEQ ID NO: 1.

* * * * *

SEQUENCE LISTING

```
Sequence total quantity: 3
SEQ ID NO: 1            moltype = DNA  length = 11061
FEATURE                 Location/Qualifiers
misc_feature            1..11061
                        note = Codon optimised dystrophin cDNA
source                  1..11061
                        mol_type = other DNA
                        organism = synthetic construct
SEQUENCE: 1
atgctgtggt gggaggaagt ggaagattgc tacgagcgcg aggacgtgca gaagaaaacc   60
ttcaccaaat gggtcaacgc ccagttcagc aagttcggca agcagcacat cgagaacctg  120
ttcagcgacc tgcaggacgg cagaaggctg ctggacctgc tggaaggcct gaccggccag  180
aagctgccca aagagaaggg cagcaccaga gtgcacgccc tgaacaacgt gaacaaggcc  240
ctgagagtgc tgcagaacaa caacgtggac ctggtcaaca tcggcagcac cgacatcgtg  300
gacggcaacc acaagctgac cctgggcctg atctggaaca tcatcctgca ctggcaggtc  360
aaaaacgtga tgaagaacat catggccggc ctgcagcaga ccaacagcga gaagatcctg  420
ctgagctggg tccgccagag caccagaaac tacccccagg tcaacgtgat caacttcacc  480
acctcttgga gcgacggcct ggccctgaac gccctgatcc acagccacag acccgacctg  540
ttcgactgga acagcgtggt ctgccagcag agcgccaccc agagactgga acacgcctto  600
aatatcgcca gataccagct gggcatcgag aagctgctgg atcccgaggc cgtggacacc  660
acctaccccg acaagaaatc catcctgatg tacatcacca gcctgttcca ggtgctgccc  720
cagcaggtct ccatcgaggc catccaggaa gtggaaatgc tgcccagacc ccccaaagtg  780
accaaagagg aacacttcca gctgcaccac cagatgcact acagccagca gatcaccgtg  840
tccctggctc agggctacga gagaaccagc agccccaagc ccagattcaa gagctacgcc  900
tacacccagg ccgcctacgt gaccaccagc gacccacca gaagcccatt ccccagccag  960
cacctggaag ccccgagga caagagcttc ggcagcagcc tgatggaaag cgaagtgaac 1020
ctggacagat accagaccgc cctggaagag gtgctgtcct ggctgctgtc cgccgaggac 1080
acactgcagg cccagggcga gatcagcaac gacgtggaag tggtcaaaga ccagttccac 1140
acccacgagg gctacatgat ggacctgacc gcccaccagg gcagagtggg caacatcctg 1200
cagctgggca gcagctgat cggcaccggc aagctgagcg aggacgaaga gacagaggtg 1260
caggaacaga tgaacctgct gaacagcaga tgggagtgcc tgagagtggc cagcatggaa 1320
aagcagagca acctgcacag agtgctgatg gatctgcaga accagaagct gaaagagctg 1380
aacgactggc tgaccaagac cgaggaacgg accagaaaga tggaagagga acccctgggc 1440
cccgacctgg aagatctgaa gagacaggtg cagcagcaca aggtgctgca ggaagatctg 1500
gaacaggaac aggtccgcgt caacagcctg acccacatgg tggtggtggt ggacgagagc 1560
agcggcgatc acgccaccgc cgctctggaa gaacagctga aggtgctggg cgacagatgg 1620
gccaacatct gccggtggac cgaggacaga tggttgctgc tgcaggacat cctgctgaag 1680
tggcagagac tgacagagga acagtgcctg ttctccgcct ggctgagcga gaaagaggac 1740
gccgtcaaca agatccacac caccggcttc aaggaccaga acgagatgct gagcagcctg 1800
cagaaactgg ccgtgctgaa ggccgatctg gaaaagaaaa agcagtccat gggcaagctg 1860
tacagcctga gcaggacct gctgtccacc ctgaagaaca gagcgtgac ccagaaaacc 1920
gaggcctggc tggacaactt cgccagatgc tgggacaacc tggtgcagaa gctggaaaag 1980
```

-continued

```
agcaccgccc agatcagcca ggccgtgacc acaacccagc cctccctgac ccagaccacc   2040
gtgatggaaa ccgtgaccac tgtgaccacc cgcgagcaga tcctggtcaa acacgcccag   2100
gaagaactgc cccctccacc ccccagaag aaaagacaga tcacagtgga cagcgagatc   2160
agaaagcggc tggatgtgga catcaccgag ctgcacagct ggatcaccag atccgaggcc   2220
gtgctgcaga gccccgagtt cgccatcttc agaaaagagg gcaacttctc cgacctgaaa   2280
gaaaagtga acgccatcga gagagagaag gccgagaagt tcagaaagct gcaggacgcc   2340
agccgctctg ctcaggctct ggtggaacag atggtcaacg agggcgtgaa cgccgacagc   2400
atcaagcagg ccagcgagca gctgaactcc agatggatcg agttctgcca gctgctgtcc   2460
gagagactga actggctgga ataccagaac aacatcattg ccttctacaa ccagctccag   2520
cagctggaac agatgaccac caccgccgag aactggctga agatccagcc caccaccccc   2580
agcgagccca ccgccatcaa gagccagctg aagatctgca aggacgaagt gaacagactg   2640
tctggcctgc agcccagat cgagaggctg aagattcagt ctatcgccct gaaagagaaa   2700
ggccagggcc ccatgttcct ggacgccgac ttcgtggcct tcaccaacca cttcaaacag   2760
gtgttctccg acgtgcaggc cagagagaaa gagctgcaga ccatcttcga caccctgccc   2820
cccatgagat accaggaaac catgagcgcc atcagaacc gggtgcagca gagcgagaca   2880
aagctgagca tccccagct gagcgtgacc gactacgaga tcatggaaca gagactgggc   2940
gagctgcagg ctctgcagtc cagtctgcag gaacagcaga gcggcctgta ctacctgagc   3000
accaccgtga aagagatgag caagaaggcc ccctccgaga tctccagaaa gtaccagagc   3060
gagttcgaag agatcgaggg cagatgcaag aagctgtcct ctcagctggt ggaacactgc   3120
cagaaactgg aagaacagat gaacaagctg cggaagatcc agaaccacat ccagaccctg   3180
aaaaagtgga tggccgaggt ggacgtgttc ctgaaagagg aatggcctgc cctgggcgac   3240
tccgagatcc tgaaaaagca gctgaacgac tgcagactgc tggtgtccga catccagaca   3300
atccagccca gcctgaactc cgtgaatgag ggcggccaga agatcaagaa cgaggccgag   3360
cctgagttcg ccagcagact ggaaaccgag ctgaaagaac tgaatacca gtgggaccac   3420
atgtgtcaga aggtctacgc ccggaaagag gccctgaagg cggcctgga aaagaccgtg   3480
tctctgcaga aagacctgtc cgagatgcac gagtggataa cccaggccga ggaagagtac   3540
ctggaaagag acttcgagta caagacccc gacgagctgc agaaagctgt ggaagaaatg   3600
aagagggcca agaagaggc ccagcagaaa gaggccaaag tcaagctgct gaccgagtcc   3660
gtgaacagcg tgatcgccca ggcccctccc gtggctcagg aagccctgaa gaagaactg   3720
gaaacactga ccaccaacta ccagtggctg tgcaccagac tgaacggcaa gtgcaagacc   3780
ctggaagaag tgtgggcctg ctggcacgag ctgctgagct acctggaaa ggccaacaag   3840
tggctgaacg aggtggaatt caagctgaaa accaccgaga acatccctgg cggcgctgaa   3900
gagatcagcg aggtgctgga cagcctgaaa aacctgatga acacagcga ggacaacccc   3960
aaccagatca gaatcctggc ccagacactg accgacggcg cgtgatgga cgagctgatc   4020
aacgaggaac tggaaacctt caacagccgg tggcgcgagc tgcacgagga agctgtgcgg   4080
agacagaaac tgctggaaca gtccatccag agcgcccagg aaaccgagaa gtccctgcac   4140
ctgatccagg aaagcctgac attcatcgac aagcagctgg ccgccatat cgccgacaag   4200
gtggacgccg cccagatgcc acaggaagct cagaagatcc agtccgacct gaccagccac   4260
gagatcagcc tggaagagat gaagaagcac aaccagggca aagaggccgc ccagagggtc   4320
ctgagccaga tcgacgtggc ccagaaaaaa ctgcaggacg tgtccatgaa gttcaggctg   4380
ttccagaagc ccgccaactt cgagcagaga ctgcaggaat ccaagatgat cctggatgaa   4440
gtgaagatgc atctgccagc cctggaaaca aagtccgtgg aacaggaagt ggtccagtcc   4500
cagctgaacc actgccgtga acctgtacaag agcctgtcc aagtgaagtc cgaggtggaa   4560
atggtcatca agaccggcag acagatcgtg cagaaaaagc agaccgagaa ccccaaagaa   4620
ctggacgaga gagtgaccgc cctgaagctg cactacaacg agctgggcgc caaagtgaca   4680
gagcggaaac agcagctgga aaagtgcctg aagctgtccc gcaagatgcg gaaagaaatg   4740
aacgtgctga cagagtggct ggctgccacc gacatgcaac tgaccaagag aagcgccgtg   4800
gaaggcatgc ccagcaacct ggactccgag gtgcatgggg gcaaggccac ccagaaagag   4860
atcgaaagc agaaggtgca cctgaagtcc atcaccgaag tgggcgaggc tctgaaaacc   4920
gtgctgggca agaaagaaac cctggtgaaa gataagctga gcctgctgaa ctctaactgg   4980
atcgccgtga ccagcagagc cgaggaatgg ctgaatctgc tgctggaata tcagaaacac   5040
atggaaacct ttgaccagaa cgtggaccac atcaccaagt ggatcatcca ggctgacacc   5100
ctgctggacg agtccgagaa gaagaaacct cagcagaaag aagatgtgct gaagagactg   5160
aaggctgagc tgaatgacat cagacccaag gtggacagca ccaggaccca ggccgccaac   5220
ctgatggcca accacggcga ccactgcaga aactggttgg aaccccagat ctccgagctg   5280
aatcacagat tcgccgccat cagccacaga atcaagacag gcaaggcag catcccctg   5340
aaaagagctgg aacagttcaa cagcgacatc cagaagctgc tggaacccct ggaagccgag   5400
atccagcagg gcgtgaacct gaaagaagag acttcaaca aggacatgaa cgaggacaac   5460
gagggcacag tgaagagct gctccagaga ggcgacaacc tgcagcagcg catcaccgac   5520
gagagaaagc gcgaggaaat caatcaag gcgcagctcc tgcagaccaa gcacaacgcc   5580
ctgaaggacc tgagatccca gagaagaaag aaggccctgg aaatcagcca ccagtggtat   5640
cagtacaaga acaggccga cgacctgctg aaatgcctgg acgacatcga gaagaagctg   5700
gctagcctgc ccgagcccag ggacgagagg aagatcaaag aaatcgaccg gaactgcag   5760
aagaagaaag aggaactgaa cgccgtccgc aggcaggccg agggcctgtc tgaagatggc   5820
gccgctatgg ccgtggaacc cacccagatc cagctgagca agagatggcg cgagatcgag   5880
agcaagttcg cccagttccg cagactgaac ttcccagga tccataccgt gcgggaagag   5940
acaatgatgg tcatgacaga ggacatgccc ctggaaatta gctacgtgcc cagcacctac   6000
ctgaccgaga tcacacacgt gtcccaggca ctgctggaaa tggaacagct gctgaatgcc   6060
cccgacctgt gcgccaagga cttcgaggat ctgttcaagc aggaagagag cctgaagaat   6120
atcaaggact ccctgcagca gtccagcggc agaatcgaca tcatccacag caagaaaaca   6180
gccgccctgc agagcgctac ccccgtggaa cgcgtgaagc tgcaggaagc actgagccag   6240
ctggacttcc agtgggagaa agtgaacaaa atgtacaagg accggcaggg cagattcgac   6300
agatccgtga aaagtggcg gagattccac tacgacatca gatcttcaa tcagtggctg   6360
acagaggccg agcagttcct gaagaagacc agatccgtgg agaactggga gcacgccaag   6420
tacaagtggt atctgaaaga actgcaggat ggcatcggcc agagacagac cgtggtccgc   6480
acactgaacg ccaccggcga agagatcatc cagcagagca gcaagaccga cgccagcatc   6540
ctgcaggaaa agctgggctc cctgaacctg agatggcagg aagtgtgcaa gcagctgagc   6600
gacagaaaga aaggctgga agaacagaag aatatcctga gcgagttcca gagggacctg   6660
aacgagttcg tgctgtggct ggaagaggct gacaatatcg cctccatccc cctggaaccc   6720
```

```
ggcaaagagc agcagctgaa agaaaaactg gaacaggtca aactgctggt ggaagaactg  6780
cctctgagac agggcagaat cctgaagcag ctgaacgaga caggcggccc tgtgctggtg  6840
tctgccccca tcagcccga ggaacaggac aaactggaaa acaaactgaa gcagacaaac  6900
ctgcagtgga tcaaggtgtc cagagccctg cccgagaagc agggggagat cgaggcccag  6960
atcaaggacc tgggccagct ggaaaaaaag ctggaagatc tggaagaaca gctcaaccat  7020
ctgctgctgt ggctgagccc catcagaaac cagctggaaa tctacaatca gcccaaccag  7080
gaaggcccct tcgacgtcaa agaaaccgag atcgccgtgc aggctaagca gcctgacgtg  7140
gaagagatcc tgagcaaggg acagcacctg tacaaagaga agcctgccac ccagcccgtg  7200
aagcgcaaac tggaagatct gtccagcgag tggaaggccg tgaaccgcct gctgcaggaa  7260
ctgagagcca agcagcccga cctggcccct ggcctgacaa caatcggcgc cagccccacc  7320
cagacagtga ccctggtcac acagcccgtg gtcacaaaag agacagccat cagcaagctg  7380
gaaatgccca gctccctgat gctggaagtg cccgccctgg ccgacttcaa cagagcctgg  7440
accgagctga ccgattggct gtctctgctg gaccaggtca tcaagtccca gcgcgtgatg  7500
gtcggcgatc tggaagatat caacgagatg atcatcaagc agaaagccac catgcaggac  7560
ctggaacaga ggcggcctca gctgaagaa ctgatcacga ccgcccagaa cctgaaaac   7620
aagaccagca accaggaagc caggaccatc atcaccgaca gaatcgagag gatccagaat  7680
cagtgggacg aagtgcagga acatctgcag aacagcgcc agcagctgaa tgagatgctg  7740
aaggacgacc cccagtggct ggaagctaaa gaagaggctg aacaggtcct gggacaggcc  7800
agagccaagc tggaatcttg gaagagggc ccctacaccg tcgacgctat ccagaagaag  7860
atcaccgaga caaaacagct ggccaaggac ctgcggcagt ggcagaccaa cgtggacgtg  7920
gccaacgacc tggctctgaa gctgctgcgg gactacagcg ccgacgacac cagaaggtg  7980
cacatgatca cagagaacat caacgcaagt tggcggagag tccacaagag agtgtctgag  8040
cgcgaggctg cactggaaga gactcacaga ctcctgcagc agttccccct ggacctggaa  8100
aaattcctgg cttggctgac cgaggctgag acaaccgcca acgtgctgca ggatgccacc  8160
agaaaagaga gactgctgga agatagcaag ggcgtgaaag aactgatgaa gcagtggcag  8220
gacctgcagc gcgaaatcga ggctcacacc gacgtgtacc acaacctgga cgagaacgcc  8280
cagaagattc tgagaagcct ggaaggcagc gacgacgccg tgctgctgca gcggagactg  8340
gacaacatga acttcaagtg gtccgagctg cgcaagaagt ctctgaacat cagatcccat  8400
ctggaagcca gcagcgacca gtggaagaga ctgcacctga gtctgcagga actgctggtc  8460
tggctgcagc tgaaggacga cgactgagc agacaggccc ccatcggcg cgatttcccc  8520
gccgtgcaga acagaacga cgtgcacaga gccttcaaga gagagctgaa aacaaaagaa  8580
cccgtgatca tgagcaccct ggaaactgtg cggatcttcc tgaccgagca gccctggaa   8640
ggactggaaa agctgtacca ggaacccaga gagctgcccc tgaggaacg ggcccagaac  8700
gtgaccccggc tgctgagaaa gcaggccgaa gaggtcaaca ccgagtggga agctgaac   8760
ctgcactccg ccgactggca gagaaagatc gacgagacac tggaacgcct gcaggaactg  8820
caggaagcta ccgacgagct ggatctgaaa ctgcggcagg ctgaagtgat caagggcagc  8880
tggcagcccg tgggggacct gctgatcgac tctctgcagg accatctgga aaaagtgaag  8940
gccctgaggg gcgagatcgc tcctctgaaa gaaaacgtgt cccacgtgaa cgacctggcc  9000
aggcagctga ccaccctggg catccagctg tcccctaca acctgagcac tctggaagat  9060
ctgaacacca gatggaagct gctgcaggtc gccgtgaag atagagtgcg gcagctgcac  9120
gaagcccaca gagacttcgg ccctgcctcc cagcacttcc tgtccacaag cgtgcagggc  9180
ccctggggaga gggccatcag ccctaacaag gtgccctact acatcaacca cgagacacag  9240
accacctgtt gggaccaccc caagatgacc gagctgatc agtctctggc cgacctgaac  9300
aatgtgcggt tcagcgccta cagaaccgct atgaagctga ggcgcctgca gaaagccctg  9360
tgcctggacc tgctgagcct gagcgccgcc tgtgacgccc tggaccagca aacctgaaa   9420
cagaatgacc agcccatgga tatcctgcag atcatcaact gcctgaccac aatctacgac  9480
aggctgaac aggaacacaa caacctgatc aacgtgccc tgtgcgtgga catgtgcctg   9540
aattggctgc tgaacgtgta cgacaccggc agaaccggca ggatcagagt gctgtcctt   9600
aagaccggca tcatcagcct gtgcaaggcc cacctggaag ataagtaccg ctatctgttt  9660
aaacaggtgg ccagctctac cggcttctgc gaccagagaa ggctgggact gctgctgcac  9720
gactccatcc agatcccag acagctggga gaggtgcct ccttcggcgg cagcaacatc   9780
gagcctagcg tgcggagctg cttccagttc gccaacaaca gcccgagat cgaagccgcc  9840
ctgttcctgg attggatgag gctggaacct cagtctatgg tctggctgcc cgtgctgcac  9900
agggtggccg ctgccgagac agccaagcac caggccaagt gcaacatctg caaagagtgc  9960
cccatcatcg gcttcagata tcggtccctg aagcacttca actacgatat ctgccagagc  10020
tgcttcttca gcggcagagt ggccaagggc cacaagatgc attaccccat ggtgaaatac  10080
tgcacccca ccaccagcgg cgaggatgtg cgggacttcg ccaaggtgct gaagaacaaa  10140
ttcaggacta agcgctactt cgctaagcac cctagaatgg gctatctgcc tgtgcagaca  10200
gtgctggaag gcgacaacat ggaaaccccc gtgacctga tcaacttttg gccgtgac   10260
agcgcacctg ccagcagtcc tcagctgagc cacgacgaca cccacagcag aatcgagcac  10320
tacgcctcca gactgccga gatggaaaac agcaacggca gctacctgaa cgacagcatc  10380
tcccccaacg agagcatcga cgacgagcat ctgctgatcc agcactactg ccagtccctg  10440
aaccaggaca gcccctgag ccagcccaga tcccctgccc agatcctgat ctccctggaa  10500
agcgagaaga gggcgagct ggaaaggatc ctggctgaac tggaaagagga aaacagaaac  10560
ctgcaggccg agtacgacag actgaagcag cagcacgagc acaagggcct gagccccctg  10620
cctagccccc ctgagatgat gccaccagc cctcagagcc caggacgc tgagctgatc    10680
gccgaggcca agctgctgag gcagcataag gccggctgg aagcccggat gcagatcctg  10740
gaagatcaca acaaacagct ggaagccag ctgcacagac tcagacagct gctggaacag  10800
ccccaggccg aggctaaagt gaacggcacc acagtgtccc ggccctccac ctccctgag   10860
agatccgaca gcagccagcc catgctgctg agagtggtcg gaagccagac cagcgacagc  10920
atgggcgaag aggatctgct gagccccct caggacacca gcagggact ggaagaagtg  10980
atggaacagc tgaacaacag cttccccagc agcagggca gaaacacccc cggcaagccc  11040
atgcgcgagg acaccatgtg a                                           11061

SEQ ID NO: 2        moltype = AA   length = 3686
FEATURE             Location/Qualifiers
source              1..3686
                    mol_type = protein
                    organism = Homo sapiens
```

SEQUENCE: 2

```
MLWWEEVEDC YEREDVQKKT FTKWVNAQFS KFGKQHIENL FSDLQDGRRL LDLLEGLTGQ    60
KLPKEKGSTR VHALNNVNKA LRVLQNNNVD LVNIGSTDIV DGNHKLTLGL IWNIILHWQV   120
KNVMKNIMAG LQQTNSEKIL LSWVRQSTRN YPQVNVINFT TSWSDGLALN ALIHSHRPDL   180
FDWNSVVCQQ SATQRLEHAF NIARYQLGIE KLLDPEDVDT TYPDKKSILM YITSLFQVLP   240
QQVSIEAIQE VEMLPRPPKV TKEEHFQLHH QMHYSQQITV SLAQGYERTS SPKPRFKSYA   300
YTQAAYVTTS DPTRSPFPSQ HLEAPEDKSF GSSLMESEVN LDRYQTALEE VLSWLLSAED   360
TLQAQGEISN DVEVVKDQFH THEGYMMDLT AHQGRVGNIL QLGSKLIGTG KLSEDEETEV   420
QEQMNLLNSR WECLRVASME KQSNLHRVLM DLQNQKLKEL NDWLTKTEER TRKMEEEPLG   480
PDLEDLKRQV QQHKVLQEDL EQEQVRVNSL THMVVVVDES SGDHATAALE EQLKVLGDRW   540
ANICRWTEDR WVLLQDILLK WQRLTEEQCL FSAWLSEKED AVNKIHTTGF KDQNEMLSSL   600
QKLAVLKADL EKKQSMGKL YSLKQDLLST LKNKSVTQKT EAWLDNFARC WDNLVQKLEK   660
STAQISQAVT TTQPSLTQTT VMETVTTVTT REQILVKHAQ EELPPPPPQK KRQITVDSEI   720
RKRLDVDITE LHSWITRSEA VLQSPEFAIF RKEGNFSDLK EKVNAIEREK AEKFRKLQDA   780
SRSAQALVEQ MVNEGVNADS IKQASEQLNS RWIEFCQLLS ERLNWLEYQN NIIAFYNQLQ   840
QLEQMTTTAE NWLKIQPTTP SEPTAIKSQL KICKDEVNRL SGLQPQIERL KIQSIALKEK   900
GQGPMFLDAD FVAFTNHFKQ VFSDVQAREK ELQTIFDTLP PMRYQETMSA IRTWVQQSET   960
KLSIPQLSVT DYEIMEQRLG ELQALQSSLQ EQQSGLYYLS TTVKEMSKKA PSEISRKYQS  1020
EFEEIEGRWK KLSSQLVEHC QKLEEQMNKL RKIQNHIQTL KKWMAEVDVF LKEEWPALGD  1080
SEILKKQLKQ CRLLVSDIQT IQPSLNSVNE GGQKIKNEAE PEFASRLETE LKELNTQWDH  1140
MCQQVYARKE ALKGGLEKTV SLQKDLSEMH EWMTQAEEEY LERDFEYKTP DELQKAVEEM  1200
KRAKEEAQQK EAKVKLLTES VNSVIAQAPP VAQEALKKEL ETLTTNYQWL CTRLNGKCKT  1260
LEEVWACWHE LLSYLEKANK WLNEVEFKLK TTENIPGGAE EISEVLDSLE NLMRHSEDNP  1320
NQIRILAQTL TDGGVMDELI NEELETFNSR WRELHEEAVR RQKLLEQSIQ SAQETEKSLH  1380
LIQESLTFID KQLAAYIADK VDAAQMPQEA QKIQSDLTSH EISLEEMKKH NQGKEAAQRV  1440
LSQIDVAQKK LQDVSMKFRL FQKPANFEQR LQESKMILDE VKMHLPALET KSVEQEVVQS  1500
QLNHCVNLYK SLSEVKSEVE MVIKTGRQIV QKKQTENPKE LDERVTALKL HYNELGAKVT  1560
ERKQQLEKCL KLSRKMRKEM NVLTEWLAAT DMELTKRSAV EGMPSNLDSE VAWGKATQKE  1620
IEKQKVHLKS ITEVGEALKT VLGKKETLVE DKLSLLNSNW IAVTSRAEEW LNLLLEYQKH  1680
METFDQNVDH ITKWIIQADT LLDESEKKKP QQKEDVLKRL KAELNDIRPK VDSTRDQAAN  1740
LMANHGDHCR KLVEPQISEL NHRFAAISHR IKTGKASIPL KELEQFNSDI QKLLEPLEAE  1800
IQQGVNLKEE DFNKDMNEDN EGTVKELLQR GDNLQQRITD ERKREEIKIK QQLLQTKHNA  1860
LKDLRSQRRK KALEISHQWY QYKRQADDLL KCLDDIEKKL ASLPEPRDER KIKEIDRELQ  1920
KKKEELNAVR RQAEGLSEDG AAMAVEPTQI QLSKRWREIE SKFAQFRRLN FAQIHTVREE  1980
TMMVMTEDMP LEISYVPSTY LTEITHVSQA LLEVEQLLNA PDLCAKDFED LFKQEESLKN  2040
IKDSLQQSSG RIDIIHSKKT AALQSATPVE RVKLQEALSQ LDFQWEKVNK MYKDRQGRFD  2100
RSVEKWRRFH YDIKIFNQWL TEAEQFLRKT QIPENWEHAK YKWYLKELQD GIGQRQTVVR  2160
TLNATGEEII QQSSKTDASI LQEKLGSLNL RWQEVCKQLS DRKKRLEEQK NILSEFQRDL  2220
NEFVLWLEEA DNIASIPLEP GKEQQLKEKL EQVKLLVEEL PLRQGRILKQ LNETGGPVLV  2280
SAPISPEEQD KLENKLKQTN LQWIKVSRAL PEKQGEIEAQ IKDLGQLEKK LEDLEEQLNH  2340
LLLWLSPIRN QLEIYNQPNQ EGPFDVKETE IAVQAKQPDV EEILSKGQHL YKEKPATQPV  2400
KRKLEDLSSE WKAVNRLLQE LRAKQPDLAP GLTTIGASPT QTVTLVTQPV VTKETAISKL  2460
EMPSSLMLEV PALADFNRAW TELTDWLSLL DQVIKSQRVM VGDLEDINEM IIKQKATMQD  2520
LEQRRPQLEE LITAAQNLKN KTSNQEARTI ITDRIERIQN QWDEVQEHLQ NRRQQLNEML  2580
KDSTQWLEAK EEAEQVLGQA RAKLESWKEG PYTVDAIQKK ITETKQLAKD LRQWQTNVDV  2640
ANDLALKLLR DYSADDTRKV HMITENINAS WRSIHKRVSE REAALEETHR LLQQFPLDLE  2700
KFLAWLTEAE TTANVLQDAT RKERLLEDSK GVKELMKQWQ DLQGEIEAHT DVYHNLDENS  2760
QKILRSLEGS DDAVLLQRRL DNMNFKWSEL RKKSLNIRSH LEASSDQWKR LHLSLQELLV  2820
WLQLKDDELS RQAPIGGDFP AVQKQNDVHR AFKRELKTKE PVIMSTLETV RIFLTEQPLE  2880
GLEKLYQEPR ELPPEERAQN VTRLLRKQAE EVNTEWEKLN LHSADWQRKI DETLERLQEL  2940
QEATDELDLK LRQAEVIKGS WQPVGDLLID SLQDHLEKVK ALRGEIAPLK ENVSHVNDLA  3000
RQLTTLGIQL SPYNLSTLED LNTRWKLLQV AVEDRVRQLH EAHRDFGPAS QHFLSTSVQG  3060
PWERAISPNK VPYYINHETQ TTCWDHPKMT ELYQSLADLN NVRFSAYRTA MKLRRLQKAL  3120
CLDDLLSLSAA CDALDQHNLK QNDQPMDILQ IINCLTTIYD RLEQEHNNLV NVPLCVDMCL  3180
NWLLNVYDTG RTGRIRVLSF KTGIIISLCKA HLEDKYRYLF KQVASSTGFC DQRRLGLLLH  3240
DSIQIPRQLG EVASFGGSNI EPSVRSCFQF ANNKPEIEAA LFLDWMRLEP QSMVWLPVLH  3300
RVAAAETAKH QAKCNICKEC PIIGFRYRSL KHFNYDICQS CFFSGRVAKG HKMHYPMVEY  3360
CTPTTSGEDV RDFAKVLKNK FRTKRYFAKH PRMGYLPVQT VLEGDNMETP VTLINFWPVD  3420
SAPASSPQLS HDDTHSRIEH YASRLAEMEN SNGSYLNDSI SPNESIDDEH LLIQHYCQSL  3480
NQDSPLSQPR SPAQILISLE SEERGELERI LADLEEENRN LQAEYDRLKQ QHEHKGLSPL  3540
PSPPEMMPTS PQSPRDAELI AEAKLLRQHK GRLEARMQIL EDHNKQLESQ LHRLRQLLEQ  3600
PQAEAKVNGT TVSSPSTSLQ RSDSSQPMLL RVVGSQTSDS MGEEDLLSPP QDTSTGLEEV  3660
MEQLNNSFPS SRGRNTPGKP MREDTM                                      3686
```

| SEQ ID NO: 3 | moltype = DNA length = 11067 |
|---|---|
| FEATURE | Location/Qualifiers |
| misc_feature | 1..11067 |
| | note = Codon optimised dystrophin cDNA including Kozak sequence |
| source | 1..11067 |
| | mol_type = other DNA |
| | organism = synthetic construct |

SEQUENCE: 3

```
gccaccatgc tgtggtggga ggaagtggaa gattgctacg agcgcgagga cgtgcagaag    60
aaaacccttca ccaaatgggt caacgcccag ttcagcaagt tcggcaagca gcacatcgag   120
aacctgttca gcgacctgca ggacggcaga aggctgctgg acctgctgga aggcctgacc   180
ggccagaagc tgcccaaaga aaagggcagc accagagtgc acgccctgaa caacgtgaac   240
aaggccctga gagtgctgca gaacaacaac gtggacctgg tcaacatcgg cagcaccgac   300
atcgtggacg gcaaccacaa gctgaccctg ggcctgatct ggaacatcat cctgcactgg   360
```

```
caggtcaaaa acgtgatgaa gaacatcatg gccggcctgc agcagaccaa cagcgagaag   420
atcctgctga gctgggtccg ccagagcacc agaaactacc cccaggtcaa cgtgatcaac   480
ttcaccacct cttggagcga cggcctggcc ctgaacgccc tgatccacag ccacagaccc   540
gacctgttcg actggaacag cgtggtctgc agcagagcg ccaccagag actgaacac     600
gccttcaata tcgccagata ccagctgggc atcgagaagc tgctggatcc cgaggacgtg   660
gacaccacct accccgacaa gaaatccatc ctgatgtaca tcaccagcct gttccaggtg   720
ctgccccagc aggtctccat cgaggccatc caggaagtgg aaatgctgcc cagaccccc   780
aaagtgacca agaggaaca cttccagctg caccaccaga tgcactacag ccagcagatc   840
accgtgtccc tggctcaggg ctacgagaga accagcagcc ccaagcccag attcaagagc   900
tacgcctaca cccaggccgc ctacgtgacc accagcgacc ccaccagaag cccattcccc   960
agccagcacc tggaagcccc cgaggacaag agcttcggca gcagcctgat ggaaagcgaa  1020
gtgaacctgg acagataccc gaccgccctg aagaggtgc tgtcctggct gctgtccgcc   1080
gaggacacac tgcaggccca gggcgagatc agcaacgacg tggaagtggt caaagaccag  1140
ttccacagcc acgagggcta catgatggac ctgaccgccc accagggcag agtgggcaac  1200
atcctgcagc tgggcagcaa gctgatcggc accggcaagc tgagcgagga cgaagagaca  1260
gaggtgcagg aacagatgaa cctgctgaac agcagatggg agtgcctgag agtgccagc   1320
atggaaaagc agagcaacct gcacagagtg ctgatggatc tgcagaacca gaagctgaaa  1380
gagctgaacg actggctgac caagaccgag gaacggacca gaaagatgga aggaaaccc   1440
ctgggcccg acctgaaga tctgaagaga caggtgcagc agcacaaggt gctgcaggaa   1500
gatctggaac aggaacaggt ccgcgtcaac agcctgaccc acatggtggt ggtggtggac  1560
gagagcagcg gcgatcacgc caccgccgct ctggaagaac agctgaaggt gctgggcgac  1620
agatgggcca acatctgccg gtggaccgag gacagatggg tgctgctgca ggacatcctg  1680
ctgaagtggc agagactgac agaggaacag tgcctgttct ccgcctggct gagcgagaaa  1740
gaggacgccg tcaacaagat ccacaccacc ggcttcaagg accagaacga gatgctgagc  1800
agcctgcaga aactggccgt gctgaaggcc gatctgaaa agaaaaagca gtccatgggc  1860
aagctgtaca gcctgaagca ggacctgctg tccaccctga gaacaaagag cgtgaccag   1920
aaaaccgagg cctggctgga caacttcgcc agatgctggg acaacctggt gcagaagctg  1980
gaaaagagca ccgcccagat cagccaggcc gtgaccacaa cccagccctc cctgacccag  2040
accaccgtga tggaaaccgt gaccactgtg accaccgcg agcagatcct ggtcaaacac   2100
gcccaggaag aactgccccc tccaccccc cagaagaaaa gacagatcac agtgacagc    2160
gagatcagaa agcggctgga tgtgacatc accgagctgc acagctggat caccagatcc   2220
gaggccgtgc tgcagagccc cgagttcgcc atcttcagaa aagagggcaa cttctccgac  2280
ctgaagaaa aagtgaacgc catcgagaga gagaaggccg agaagttcag aaagctgcag   2340
gacgccagcc gctctgctca ggctctggtg gaacagatgg tcaacgaggg cgtgaacgc    2400
gacagcatca agcaggccag cgagcagctg aactccagat ggatcgagtt ctgccagctg  2460
ctgtccgaga gactgaactg gctggaatac cagaacaaca tcattgcctt ctacaaccag  2520
ctccagcagc tggaacagat gaccaccac gccgagaact ggctgaagat ccagcccacc   2580
accccagcg agccaccgc catcaagagc agctgaaga tctgcaagga cgaagtgaac    2640
agactgctg gcctgcagcc ccagatcgag gcctgaaa ttcagtctat cgccctgaaa    2700
gagaaaggcc agggccccat gttcctggac gccgacttcg tggccttcac caaccacttc  2760
aaacaggtgt tctccgacgt gcaggccaga gagaaagagc tgcagaccat cttcgacacc  2820
ctgccccca tgagataccca ggaaaccatg agcgccatca aacctgggt gcagcagagc   2880
gagacaaagc tgagcatccc ccagtcgac gtgaccgacc agagatcat ggaacagaga   2940
ctgggcgagc tgcaggctct gcagtccagt ctgcaggaac agcagagcgg cctgtactac  3000
ctgagcacca ccgtgaaaga gatgagcaag aaggccccct ccgagatctc cagaaagtac  3060
cagagcgagt tcgaagagat cgagggcaga tggaagaagc tgtcctctca gctggtggaa  3120
cactgccaga aactggaaga acagatgaac aagctgcgga agatccagaa ccacatccag  3180
accctgaaaa agtggatggc cgaggtggac gtgttcctga agaggaatg gcctgccctg  3240
ggcgactccg agatcctgaa aaagcagctg aagcagtgca gactgctggt gtccgacatc  3300
cagacaatcc agcccagcct gaactccgtg aatgagggcg ccagaagat caagaacgag   3360
gccgagcctg agttcgccag cagactgaa accgagctga agaactgaa taccccagtgg  3420
gaccacatgt gtcagcaggt ctacgcccgg aaagaggccc tgaagggcgg cctgaaaag   3480
accgtgtctc tgcagaaaga cctgtccgag atgcacgagt ggatgaccca ggccgaggaa  3540
gagtacctgg aaagagactt cgagtacaag accccgacg agctgcagaa agctgtggaa   3600
gaaatgaaga gggccaaaga gagggccag cagaaagagg caaagtcaa gctgctgacc    3660
gagtccgtga acagcgtgat cgcccaggcc cctcccgtgg ctcaggaagc cctgaagaaa  3720
gaactggaaa cactgaccac caactaccag tggctgtgca ccagactgaa cggcaagtgc  3780
aagaccctga agaagtgtg gcctgctgg cacgagctgc tgagctacct ggaaaaggcc   3840
aacaagtggc tgaacgaggt ggaattcaag ctgaaaacca ccgagaacat ccctggcggc   3900
gctgaagaga tcagcaggt gctgacagc ctgaaaacc tgatgagaca cagcgaggac    3960
aaccccaacc agatcagaat cctgcccag acactgaccg acggcggcgt gatggacgag   4020
ctgatcaacg aggaactgga aaccttcaac agccggtggc gcgagctgca cgaggaagct  4080
gtgcgggaga gaaactgct ggaacagtcc atccagagcc ccaggaaac cgagaagtcc   4140
ctgcacctga tccaggaag cctgacattc atcgacaagc agctggcccg ctatatcgct   4200
gacaaggtgg acgccgccca gatgccacac gaagctcaga agatccagtc cgacctgacc  4260
agccacgaga tcagcctgga agagatgaag aagcacaacc agggcaaaga ggccgcccag  4320
agggtcctga gccagatcga cgtggcccag aaaaaactgc aggacgtgtc catgaagttc  4380
aggctgtcc agaagcccgc caacttcgag cagagactgc aggaatccaa gatgatcctg  4440
gatgaagtga gatgcatct gccagccctg gaacaaaagt ccgtggaaca ggaagtgctg  4500
cagtcccagc tgaaccactg cgtgaacctg tacaagagcc tgtccgaagt gaagtccgag  4560
gtggaaatgt tcatcaagac cggcagacag atcgtcagaa aaagcagac cgagaaccc   4620
aaagaactgg acgagagagt gaccgccctg aagctgcact acaacgagct gggcgccaaa  4680
gtgacagagc ggaaacagca gctggaaaag tgcctgaagc tgtcccgcaa gatgcggaaa  4740
gaaatgaacg tgctgacaga gtggctggct gccaccgaca tggaactgac caagagaagc  4800
gccgtggaag gcatgccag caacctggac tccgaggtgg catgggcaa ggccaccag    4860
aaagagatcc aaaagcagaa ggtgcacctg aagtccatca ccgaagtggg cgaggctctg  4920
aaaaccgtgc tgggcaagaa agaaaccctg gtggaagata gctgagcct gctgaactct  4980
aactggatcc ccgtgaccag cagagccgag gaatggctga atctgctgct ggaatatcag  5040
aaacacatgg aaaccttgta ccagaacgtg gaccacatca ccagtggat catccaggct  5100
```

```
gacaccctgc tggacgagtc cgagaagaag aaacctcagc agaaagaaga tgtgctgaag   5160
agactgaagg ctgagctgaa tgacatcaga cccaaggtgg acagcaccag ggaccaggcc   5220
gccaacctga tggccaacca cggcgaccac tgcagaaaac tggtggaacc ccagatctcc   5280
gagctgaatc acagattcgc cgccatcagc cacagaatca agacaggcaa ggccagcatc   5340
cccctgaaag agctggaaca gttcaacagc gacatccaga agctgctgga accccctgga   5400
gccgagatcc agcagggcgt gaacctgaaa gaagaggact tcaacaagga catgaacgag   5460
gacaacgagg gcacagtgaa agagctgctc cagagaggcg acaacctgca gcagcgcatc   5520
accgacgaga gaaagcgcga ggaaatcaag atcaagcagc agctcctgca gaccaagcac   5580
aacgccctga aggacctgag atcccagaga agaaagaagg ccctggaaat cagccaccag   5640
tggtatcagt acaagagaca ggccgacgac ctgctgaaat gcctggacga catcgagaag   5700
aagctggcta gcctgcccga gcccaggggac gagaggaaga tcaaagaaat cgaccgggaa   5760
ctgcagaaga gaaagagga actgaacgcc gtccgcaggc aggccgaggg cctgtctgaa   5820
gatggcgccg ctatggccgt ggaacccacc cagatccagc tgagcaagag atggcgcgag   5880
atcgagagca agttcgccca gttccgcaga ctgaacttcg cccagatcca taccgtgcgg   5940
gaagagacaa tgatggtcat gacagaggac atgcccctgg aaattagcta cgtgcccagc   6000
acctacctga ccgagatcac acacgtgtcc caggcactgc tggaagtgga acagctgctg   6060
aatgccccga acctgtgcgc caaggacttc gaggatctgt tcaagcagga agagagcctg   6120
aagaatatca aggactcccct gcagcagtcc agcggcagaa tcgacatcat ccacagcaag   6180
aaaacagccg ccctgcagag cgctaccccc gtgaacgcg tgaagctgca ggaagcactg   6240
agccagctgg acttccagtg ggagaaagtg aacaaaatgt acaaggaccg gcagggcaga   6300
ttcgacagat ccgtggaaaa gtggcggaga ttccactacg acatcaagat cttcaatcag   6360
tggctgacag aggccagca gttcctgaga aagacccaga tccctgagaa ctgggagcac   6420
gccaagtaca agtggtatct gaaagaactg caggatggca tcggccagag acagaccgtg   6480
gtccgcacac tgaacgccac cggcaagaga atcatccagc agagcagcaa gaccgacgcc   6540
agcatcctgc aggaaaagct gggctccctg aacctgagat ggcaggaagt gtgcaagcag   6600
ctgagcgaca gaaagaaaag gctgaagaa cagaagaata tcctgagcga gttccagagg   6660
gacctgaacg agttcgtgct gtggctgaa gaggctgaca atatcgcctc catcccectg   6720
gaacccggca agagcagca gctgaaagaa aaactggaac aggtcaaact gctggtggaa   6780
gaactgcctc tgacacaggg cagaatcctg aagcagctga cgagacagg cggccctgtg   6840
ctggtgtctg cccccatcag ccccgaggaa caggacaaac tggaaaacaa actgaagcag   6900
acaaacctgc agtggatcaa ggtgtccaga gccctgcccg agaagcaggg ggagatcgaa   6960
gcccagatca aggacctggg ccagctgaaa aaaagctgg aagatctgga agaacagctc   7020
aaccatctgc tgctgtggct gagccccatc agaaaccagc tggaaatcta caatcagccc   7080
aaccaggaag gccccttcga cgtcaaagaa accgagatcg ccgtgcaggc taagcagcct   7140
gacgtggaag atcctgag caagggacag cacctgtaca aagagaagcc tgccacccag   7200
cccgtgaagc gcaaactgga agatctgtcc agcgagtgga aggccgtgaa ccgcctgctg   7260
caggaactga gagccaagca gcccgacctg gcccctggcc tgacaacaat cggcgccagc   7320
cccacccaga cagtgaccct ggtcacacag cccgtggtca caaagagac agccatcagc   7380
aagctggaaa tgcccagctc cctgatgctg gaagtgcccg ccctggccga cttcaacaga   7440
gcctggaccg agctgaccga ttggctgtct ctgctgaccc aggtcatcaa gtcccagcgc   7500
gtgatggtcg gcgatctgga agatatcaac gagatgatca tcaagcagaa agccaccatg   7560
caggacctgg aacagaggcg gcctcagctg gaagaactga tcacagccgc ccagaacctg   7620
aaaaacaaga ccagcaacca ggaagccagg accatcatca ccgacagaat cgagaggatc   7680
cagaatcagt gggacgaagt gcaggaacat ctgcagaaca gacgccagca gctgaatgag   7740
atgctgaagg acagcaccca gtggctgaa gctaaagaag aggctgaaca ggtcctggga   7800
caggccgagg ccaagctgga atcttggaaa gagggccct acaccgtcga cgctatccag   7860
aagaagatca ccgagacaaa acagctgctc aaggacctgc ggcagtggca gaccaacgtg   7920
gacgtggcca acgacctggc tctgaagctg ctgcgggact acagcgccga cgacaccaga   7980
aaggtgcaca tgatcacaga gaacatcaac gcaagttggc ggagcatcca aagagagtg   8040
tctgagcgcg aggctgcact ggaagagact cacagactcc tgcagcagtt cccccctggac   8100
ctggaaaaat tcctggcttg gctgaccgag gctgagacaa cccaacgt gctgcaggat   8160
gccaccagaa aagagagact gctggaagat agcaagggcg tgaaagaact gatgaagcag   8220
tggcaggacc tgcagggcga aatcgaggct cacaccgacg tgtaccacaa cctgacgag   8280
aacagccaga agattctgag aagctgcaa ggcagcgacg acgccgtgct gctgcagcgg   8340
agactggaca acatgaactt caagtggtcc gagctgcgca agaagtctct gaacatcaga   8400
tcccatctgg aagccagcag cgaccagtgg aagagactgc acctgagtct gcaggaactg   8460
ctggtctgc tgcagctgaa ggacgacgag ctgagcagac aggcccccat cggcggcgat   8520
ttccccgccg tgcagaaaca gaacgacgtg cacagagcct tcaagagaga gctgaaaaca   8580
aaagaaccc tgatcatgag caccctggaa actgtgcgga tcttcctgac cgagcagccc   8640
ctggaaggac tgaaaagct gtaccaggaa cccagagc tgccccctga ggaacgggcc   8700
cagaacgtga cccggctgct gagaaagcag gccgaagagg tcaacaccga gtgggagaag   8760
ctgaacctgc actccgccga ctggcagaga aagatcgacg agacactgga acgcctgcag   8820
gaactgcagg aagctaccga cgagctggat ctgaaactgc ggcaggctga agtgatcaag   8880
ggcagctggc agcccgctgg gatcgctctc tgcaggacca tctgaaaaa   8940
gtgaaggccc tgaggggcga gatcgctcct ctgaaagaaa acgtgtccca cgtgaacgac   9000
ctggccaggc agctgaccac cctgggcatc cagctgtccc cctacaacct gagcactctg   9060
gaagatctga caccagatg gaagctgctg caggtcgccg tggaagatag agtgcggcag   9120
ctgcacgaag cccacagaga cttcggccct gcctcccagc acttcctgtc cacaagcgtg   9180
cagggcccct gggagagggc catcagccct aacaaggtgc cctactacat caaccacgag   9240
acacagacca cctgttggga ccaccccaag atgaccgagc tgtatcagtc tctggccgac   9300
ctgaacaatg tgcggttcag cgccctacaga accgctatga agctgaggcg cctgcagaaa   9360
gccctgtgcc tggacctgct gagcctgagc gccgcctgtg acgccctgga ccagcacaac   9420
ctgaaacaga atgaccagcc catggatatc ctgcagatca tcaactgcct gaccacaatc   9480
tacgacgtgc tggaacagga acacaacaac ctggtcaacg tgcccctgtg cgtggacatg   9540
tgcctgaatt ggctgctgaa cgtgtacgac accggcagaa ccggcaggat cagagtgctg   9600
tcctttaaga ccggcatcat cagcctgtgc aaggcccacc tggaagataa gtaccgctat   9660
ctgtttaaac aggtggccag ctctaccggc ttctgcgacc agagaggct gggactgctg   9720
ctgcacgact ccatccagat ccccagacag ctgggagagg tggcctcctt cggcggcagc   9780
aacatcgagc ctagcgtgcg gagctgcttc cagttcgcca acaacaagcc cgagatcgaa   9840
```

```
gccgccctgt tcctggattg gatgaggctg gaacctcagt ctatggtctg gctgcccgtg    9900
ctgcacaggg tggccgctgc cgagacagcc aagcaccagg ccaagtgcaa catctgcaaa    9960
gagtgcccca tcatcggctt cagatatcgg tccctgaagc acttcaacta cgatatctgc   10020
cagagctgct tcttcagcgg cagagtggcc aagggccaca agatgcatta ccccatggtg   10080
gaatactgca cccccaccac cagcggcgag gatgtgcggg acttcgccaa ggtgctgaag   10140
aacaaattca ggactaagcg ctacttcgct aagcaccctg gaatgggcta tctgcctgtg   10200
cagacagtgc tggaaggcga caacatgaag accccgtga ccctgatcaa cttttggccc   10260
gtggacagcg cacctgccag cagtcctcag ctgagccacg acgacaccca cagcagaatc   10320
gagcactacg cctccagact ggccgagatg gaaaacagca acggcagcta cctgaacgac   10380
agcatctccc ccaacgagag catcgacgac gagcatctgc tgatccagca ctactgccag   10440
tccctgaacc aggacagccc cctgagccag cccagatccc ctgcccagat cctgatctcc   10500
ctggaaagcg aggaaagagg cgagctgaaa aggatcctgg ctgacctgga agaggaaaac   10560
agaaacctgc aggccgagta cgacagactg aagcagcagc acgagcacaa gggcctgagc   10620
cccctgccta gccccctga gatgatgccc accagccctc agagccccag ggacgctgag   10680
ctgatcgccg aggccaagct gctgaggcag cataagggcc ggctggaagc ccggatgcag   10740
atcctggaag atcacaacaa acagctgaa agccagctgc acagactcag acagctgctg   10800
gaacagcccc aggccgaggc taaagtgaac ggcaccacag tgtccagccc ctccacctcc   10860
ctgcagagat ccgacagcag ccagcccatg ctgctgagag tggtcggaag ccagaccagc   10920
gacagcatgg gcgaagagga tctgctgagc cccctcagg acaccagcac aggactggaa   10980
gaagtgatgg aacagctgaa caacagcttc cccagcagca gaggcagaaa cacccccggc   11040
aagcccatgc gcgaggacac catgtga                                       11067
```